(12) United States Patent
Freeman et al.

(10) Patent No.: US 12,211,611 B2
(45) Date of Patent: Jan. 28, 2025

(54) SURGERY VISUALIZATION THEATRE

(71) Applicant: Raytrx, LLC, Tulsa, OK (US)

(72) Inventors: Michael Hayes Freeman, Tulsa, OK (US); Mitchael C. Freeman, Sapulpa, OK (US); Jordan Boss, Tulsa, OK (US); Brian Santee, Tulsa, OK (US); Montgomery H. F. Freeman, Dana Point, CA (US); Thomas A. Finley, Tulsa, OK (US); Linda Lam, Sierra Madre, CA (US); Victoria M. McArtor, Tulsa, OK (US); Steven Yeager, Colorado Springs, CO (US); David Kessler, Rochester, NY (US); Ian Oswald, Stillwater, OK (US)

(73) Assignee: RAYTRX, LLC, Tulsa, OK (US)

( * ) Notice: Subject to any disclaimer, the term of this patent is extended or adjusted under 35 U.S.C. 154(b) by 0 days.

(21) Appl. No.: 18/606,941

(22) Filed: Mar. 15, 2024

(65) Prior Publication Data
US 2024/0266033 A1 Aug. 8, 2024

Related U.S. Application Data

(63) Continuation of application No. 17/307,771, filed on May 4, 2021, now Pat. No. 12,062,430, which is a
(Continued)

(51) Int. Cl.
*G16H 30/40* (2018.01)
*A61B 3/00* (2006.01)
(Continued)

(52) U.S. Cl.
CPC ........... *G16H 30/40* (2018.01); *A61B 3/0025* (2013.01); *A61B 3/024* (2013.01); *A61B 3/032* (2013.01);
(Continued)

(58) Field of Classification Search
CPC ........ G16H 10/60; G16H 30/20; G16H 30/40; G16H 50/20; G16Z 99/00; A61B 3/024;
(Continued)

(56) References Cited

U.S. PATENT DOCUMENTS

| 6,449,103 B1 | 9/2002 | Charles |
| 7,639,208 B1 | 12/2009 | Ha et al. |

(Continued)

FOREIGN PATENT DOCUMENTS

| CN | 105188516 A | 12/2015 |
| EP | 4 106 664 A1 | 12/2021 |

(Continued)

OTHER PUBLICATIONS

Loshin, David S. et al., The Programmable Remapper: Clinical Applications for Patients with Field Defects, Optometry and Vision Science, received Nov. 4, 1988, revision received Mar. 3, 1989, pp. 389-395, vol. 66, No. 6, US.

(Continued)

*Primary Examiner* — Mark Edwards
(74) *Attorney, Agent, or Firm* — Howard & Howard Attorneys PLLC

(57) ABSTRACT

An augmented/extended reality (AXR) headset for use with a surgery visualization system is described herein. The AXR headset includes a wearable support frame, one or more forward-facing cameras pivotably mounted to the wearable support frame, an imaging system mounted to the wearable support frame, and a control logic processor coupled to the one or more front facing cameras and the image generator, and programmed to execute an algorithm including the steps of receiving image data from the one or more forward-facing cameras and operating the image generator to display the received image data onto the curved mirror.

18 Claims, 25 Drawing Sheets

Related U.S. Application Data continuation-in-part of application No. 17/182,022, filed on Feb. 22, 2021, now Pat. No. 11,628,038.

(60) Provisional application No. 63/019,796, filed on May 4, 2020, provisional application No. 63/005,202, filed on Apr. 3, 2020, provisional application No. 62/986,461, filed on Mar. 6, 2020, provisional application No. 62/979,999, filed on Feb. 21, 2020.

(51) Int. Cl.

| | | |
|---|---|---|
| *A61B 3/024* | (2006.01) | |
| *A61B 3/032* | (2006.01) | |
| *A61B 3/12* | (2006.01) | |
| *A61F 9/08* | (2006.01) | |
| *G16H 10/60* | (2018.01) | |
| *G16H 30/20* | (2018.01) | |
| *G16H 50/20* | (2018.01) | |
| *G16Z 99/00* | (2019.01) | |

(52) U.S. Cl.
CPC ............... *A61B 3/12* (2013.01); *G16H 10/60* (2018.01); *G16H 30/20* (2018.01); *G16H 50/20* (2018.01); *G16Z 99/00* (2019.02); *A61F 9/08* (2013.01)

(58) Field of Classification Search
CPC ......... A61B 3/032; A61B 3/12; A61B 3/0025; A61F 9/08
USPC ....................................................... 351/224
See application file for complete search history.

(56) References Cited

U.S. PATENT DOCUMENTS

| | | |
|---|---|---|
| 8,135,227 B2 | 3/2012 | Lewis et al. |
| 8,311,328 B2 | 11/2012 | Spruck |
| 8,350,898 B2 | 1/2013 | Chang et al. |
| 8,494,298 B2 | 7/2013 | Lewis et al. |
| 8,579,194 B2 | 11/2013 | Boss et al. |
| 8,771,805 B2 | 7/2014 | Laude et al. |
| 8,798,756 B2 | 8/2014 | McClure et al. |
| 8,812,120 B2 | 8/2014 | Greenberg et al. |
| 8,831,734 B2 | 9/2014 | Nanduri et al. |
| 8,831,745 B2 | 9/2014 | Hung et al. |
| 8,874,224 B2 | 10/2014 | Greenberg et al. |
| 8,874,239 B2 | 10/2014 | Greenberg et al. |
| 8,886,329 B2 | 11/2014 | Greenberg et al. |
| 8,912,979 B1 | 12/2014 | Gomez |
| 8,934,983 B2 | 1/2015 | Greenberg et al. |
| 8,954,157 B2 | 2/2015 | Faraji et al. |
| 8,976,086 B2 | 3/2015 | Hilkes |
| 9,002,462 B2 | 4/2015 | McClure et al. |
| 9,042,985 B2 | 5/2015 | Marsh et al. |
| 9,044,590 B2 | 6/2015 | Greenberg et al. |
| 9,044,591 B2 | 6/2015 | Greenberg et al. |
| 9,050,468 B2 | 6/2015 | Greenberg et al. |
| 9,061,150 B2 | 6/2015 | Greenberg et al. |
| 9,072,888 B2 | 7/2015 | Greenberg et al. |
| 9,072,900 B2 | 7/2015 | Caspi et al. |
| 9,078,739 B2 | 7/2015 | Greenberg et al. |
| 9,084,895 B2 | 7/2015 | Greenberg et al. |
| 9,089,690 B2 | 7/2015 | Greenberg et al. |
| 9,089,701 B2 | 7/2015 | Zhou et al. |
| 9,089,702 B2 | 7/2015 | Dorn et al. |
| 9,095,709 B2 | 8/2015 | McClure et al. |
| 9,095,710 B2 | 8/2015 | Horsager et al. |
| 9,095,722 B2 | 8/2015 | Mech et al. |
| 9,097,891 B2 | 8/2015 | Border et al. |
| 9,651,784 B2 | 5/2017 | Osterhout |
| 9,651,786 B1 | 5/2017 | Browne |
| 9,955,862 B2 | 5/2018 | Freeman et al. |
| 10,111,583 B1 | 10/2018 | Freeman et al. |
| 10,149,958 B1 | 12/2018 | Tran et al. |
| 10,323,904 B1 | 6/2019 | Batten |
| 10,345,768 B2 | 7/2019 | Fullam et al. |
| 10,638,080 B2 | 4/2020 | Ovchinnikov et al. |
| 10,732,407 B1 * | 8/2020 | Wood ....................... G02B 5/30 |
| 10,874,297 B1 | 12/2020 | Freeman et al. |
| 2002/0063807 A1 | 5/2002 | Margulis |
| 2002/0082498 A1 | 6/2002 | Wendt et al. |
| 2003/0223038 A1 | 12/2003 | Alster et al. |
| 2005/0036109 A1 | 2/2005 | Blum et al. |
| 2005/0168569 A1 | 8/2005 | Igarashi |
| 2005/0280603 A1 | 12/2005 | Aughey et al. |
| 2006/0087746 A1 | 4/2006 | Lipow |
| 2006/0238710 A1 | 10/2006 | Dick et al. |
| 2007/0121070 A1 | 5/2007 | Alster et al. |
| 2007/0273983 A1 * | 11/2007 | Hebert ............... G02B 27/0172 359/708 |
| 2009/0086313 A1 | 4/2009 | Zimmer |
| 2009/0123036 A1 | 5/2009 | Huang et al. |
| 2009/0128834 A1 | 5/2009 | Matsuhira |
| 2009/0218400 A1 | 9/2009 | Boss et al. |
| 2010/0011959 A1 | 1/2010 | Marra |
| 2010/0079356 A1 | 4/2010 | Hoellwarth |
| 2010/0149073 A1 | 6/2010 | Chaum et al. |
| 2010/0254017 A1 | 10/2010 | Martins |
| 2010/0277471 A1 | 11/2010 | Beato et al. |
| 2011/0043644 A1 | 2/2011 | Munger et al. |
| 2012/0068913 A1 | 3/2012 | Bar-Zeev et al. |
| 2012/0206335 A1 * | 8/2012 | Osterhout ............... G06F 1/163 345/156 |
| 2012/0281181 A1 | 11/2012 | Chen et al. |
| 2012/0326948 A1 | 12/2012 | Crocco |
| 2013/0099700 A1 | 4/2013 | Kreye et al. |
| 2013/0155507 A1 | 6/2013 | Ryu et al. |
| 2013/0162632 A1 | 6/2013 | Varga et al. |
| 2013/0162673 A1 | 6/2013 | Bohn |
| 2013/0172902 A1 | 7/2013 | Lightcap et al. |
| 2013/0178868 A1 | 7/2013 | Roh |
| 2013/0194254 A1 | 8/2013 | Miyoshi et al. |
| 2013/0200595 A1 | 8/2013 | Mackay et al. |
| 2013/0215147 A1 | 12/2013 | Hilkes et al. |
| 2013/0329184 A1 | 12/2013 | Barzak et al. |
| 2013/0329190 A1 | 12/2013 | Lewis et al. |
| 2013/0335543 A1 | 12/2013 | Hilkes et al. |
| 2014/0002587 A1 | 1/2014 | Aguren |
| 2014/0002597 A1 | 1/2014 | Aguren |
| 2014/0063054 A1 | 3/2014 | Osterhout et al. |
| 2014/0094655 A1 | 4/2014 | Newman |
| 2014/0098226 A1 | 4/2014 | Pletcher |
| 2014/0160264 A1 | 6/2014 | Taylor et al. |
| 2014/0214122 A1 | 7/2014 | Nanduri et al. |
| 2014/0232645 A1 | 8/2014 | Ali et al. |
| 2014/0243971 A1 | 8/2014 | Pugh et al. |
| 2014/0275760 A1 | 9/2014 | Lee et al. |
| 2014/0283429 A1 | 9/2014 | Sullivan et al. |
| 2014/0306866 A1 | 10/2014 | Miller et al. |
| 2015/0005785 A1 | 1/2015 | Olson |
| 2015/0084841 A1 | 3/2015 | Hilkes |
| 2015/0193984 A1 | 7/2015 | Bar-Zeev et al. |
| 2015/0201532 A1 | 7/2015 | Osterhout et al. |
| 2015/0355481 A1 | 12/2015 | Hilkes et al. |
| 2015/0362733 A1 | 12/2015 | Spivack |
| 2015/0378074 A1 | 12/2015 | Kollin et al. |
| 2016/0027216 A1 | 1/2016 | da Veiga et al. |
| 2016/0037849 A1 | 2/2016 | Shearman et al. |
| 2016/0055822 A1 | 2/2016 | Bell |
| 2016/0091968 A1 | 3/2016 | Angelo et al. |
| 2016/0183779 A1 | 6/2016 | Ren et al. |
| 2016/0196694 A1 | 7/2016 | Lindeman |
| 2016/0247418 A1 | 8/2016 | Folzenlogen et al. |
| 2016/0252325 A1 | 9/2016 | Sammut et al. |
| 2016/0262608 A1 | 9/2016 | Krueger |
| 2016/0267720 A1 | 9/2016 | Mandella et al. |
| 2016/0270648 A1 | 9/2016 | Freeman et al. |
| 2016/0270656 A1 | 9/2016 | Samec et al. |
| 2016/0361643 A1 * | 12/2016 | Allin ................... A63F 13/5255 |
| 2016/0377871 A1 | 12/2016 | Kress et al. |
| 2016/0379593 A1 | 12/2016 | Borenstein et al. |
| 2017/0007351 A1 | 1/2017 | Yu |
| 2017/0010469 A1 | 1/2017 | Samec et al. |

(56) References Cited

U.S. PATENT DOCUMENTS

| | | |
|---|---|---|
| 2017/0011706 A1 | 1/2017 | Namkung et al. |
| 2017/0068119 A1 | 3/2017 | Antaki et al. |
| 2017/0094167 A1 | 3/2017 | Riedel |
| 2017/0236332 A1 | 8/2017 | Kipman et al. |
| 2017/0242253 A1 | 8/2017 | Benesh |
| 2017/0257619 A1* | 9/2017 | Kashima ............ A61B 1/00188 |
| 2017/0293380 A1 | 10/2017 | Chauveau et al. |
| 2017/0323615 A1 | 11/2017 | Hazra et al. |
| 2018/0024369 A1* | 1/2018 | Kato ..................... G02C 11/10 359/13 |
| 2018/0045964 A1 | 2/2018 | Jones et al. |
| 2018/0116742 A1 | 5/2018 | Dell et al. |
| 2018/0125340 A1 | 5/2018 | Ishikawa |
| 2018/0153632 A1 | 6/2018 | Tokarchuk et al. |
| 2018/0250085 A1 | 9/2018 | Simi et al. |
| 2018/0325618 A1 | 11/2018 | Justin et al. |
| 2019/0339528 A1 | 11/2019 | Freeman et al. |
| 2019/0353457 A1 | 11/2019 | Northrup |
| 2019/0359351 A1 | 11/2019 | Fisher et al. |
| 2020/0030054 A1 | 1/2020 | Okawara |
| 2020/0038120 A1 | 2/2020 | Ziraknejad et al. |
| 2020/0281670 A1 | 9/2020 | Moskowitz |
| 2021/0022599 A1 | 1/2021 | Freeman et al. |
| 2021/0149173 A1 | 5/2021 | Knoblich et al. |

FOREIGN PATENT DOCUMENTS

| | | |
|---|---|---|
| EP | 4 052 647 A1 | 9/2022 |
| JP | 09245195 | 9/1997 |
| JP | 5571901 B2 | 8/2014 |
| KR | 10-2013-0082637 | 7/2013 |
| KR | 10-2014-0112207 | 9/2014 |
| KR | 10-2018-0068351 | 6/2018 |
| WO | 2014/140849 A2 | 9/2014 |
| WO | 2016/133644 | 8/2016 |
| WO | 2017/020081 A1 | 2/2017 |
| WO | 2017/064301 | 4/2017 |
| WO | 2018/067611 | 4/2018 |
| WO | 2020/014707 A1 | 1/2020 |
| WO | 2020/075501 A1 | 4/2020 |

OTHER PUBLICATIONS

Wrobleswki, Dariusz et al., Testing of Visual Field with Virtual Reality Goggles in Manual and Visual Grasp Modes, Biomed Research International, vol. 2014 (2014), Article ID 206082, pp. 1-7, http://www.hindawi.com/journals/bmri/2014/206082.

Hainich, Rolf R. et al., Near-Eye Displays (NED), Displays: Fundamentals and Applications, Second Edition, 2016, XP093124959, pp. 417-494.

\* cited by examiner

66

SURGERY VISUALIZATION THEATRE

CROSS REFERENCE TO RELATED APPLICATIONS

This application is a continuation of U.S. patent application Ser. No. 17/307,771, filed May 4, 2021, which claims the benefit of U.S. Provisional Patent Application Ser. No. 63/019,796, filed May 5, 2020, and which is continuation-in-part of U.S. patent application Ser. No. 17/182,022, filed Feb. 22, 2021 (now U.S. Pat. No. 11,628,038, issued Apr. 18, 2023), which claims the benefit of U.S. Provisional Patent Application Ser. No. 62/979,999, filed Feb. 21, 2020, U.S. Provisional Patent Application Ser. No. 62/986,461, filed Mar. 6, 2020, U.S. Provisional Patent Application Ser. No. 63/005,202, filed Apr. 3, 2020, and U.S. Provisional Patent Application Ser. No. 63/019,796, filed May 4, 2020, the disclosures of which are hereby incorporated by reference in their entirety for all purposes.

COPYRIGHT NOTICE

A portion of this disclosure contains material that is subject to copyright or trademark protection. The copyright and trademark owner has no objection to the facsimile reproduction by anyone of this patent document as it appears in the U.S. patent and Trademark Office, patent file or records, but reserves all copyrights whatsoever in the subject matter presented herein. The trademark names of the systems herein are those selected by the inventors but are not exclusive of names which could be used.

FIELD OF THE INVENTION

This invention relates generally to a surgery visualization theatre, with optional methods to view a surgery video feed, and more particularly, but not by way of limitation, to a surgery visualization theatre featuring an augmented reality headset, a virtual reality viewport, a 3D autostereoscopic no glasses monitor, and an all-digital 12K 3D microscope wherein the virtual reality viewport, autostereoscopic monitor, and 3D microscope are configured on cobotic arms. While the preferred embodiment for the surgery visualization theatre would provide all three digital viewing options, the system could comprise less than all three viewing options, or each of the viewing options may be used independently of the others. Further, while this system was first originated for medical and surgery applications, it could also be used in other sectors, for other non-surgical applications such as industrial applications where a real-time video feed is necessary, and several viewing options for the viewer or operator are advantageous.

BACKGROUND OF THE INVENTION

There is a need for surgeons to be able to access real-time and pre-recorded computer-generated and/or camera images in the operating room. In addition, the operating room (OR) healthcare professionals need multiple viewing ports providing 3D surgery site information to such personnel for them to accomplish their OR tasks. Since the 1800s, surgeons have relied on the standard optical microscope (SOM), which uses multiple lenses in a dual tube configuration to create optical zoom and magnification designed to be viewed by a human operator. In addition, OR personnel also need to be able to recall electronic medical record (EMR) information during surgery, such as 3D MRI's, CT scans, and other imaging, which currently is done through 2D viewing on a light board in the operating room or through multiple monitors throughout the OR, or in adjacent clinic/diagnostic rooms. In the recent past, some large medical device manufactures have introduced SOM's that project video through a wired connection onto 3D monitors which require the OR personnel to wear polarized 3D glasses, and which require the surgeon to strain, crane, or lean for hours to observe. As the 3D glasses are polarized up to 50%, this is somewhat akin to having a surgeon wearing sunglasses to surgery and does not provide the surgeon with good ergonomics or state-of-the-art digital technologies.

Recent trends in the field have shown some SOM manufacturers adding digital imaging to the legacy equipment, but this means that an already large SOM becomes larger and more cumbersome and takes ever larger highly-valued surgery space away from the OR personnel.

Further, a typical surgical SOM is traditionally limited by the resolution of the observer's eye with an upper bound of the retinal resolution. In contrast, a digital microscope can use algorithms to detect features that are imperceptible to the eye. Moreover, the typical SOM does not have the same zoom range, typically only 6×, as a digital microscope because a digital microscope has both optical and digital zoom, which can achieve magnifications of up to 500×.

Beyond this, a SOM cannot provide the best three-dimensional renderings. Although when using a stereo SOM, an operator can see 3D depth owing to the fact that the operator is receiving two slightly different views of the object under study through the ocular eye-pieces, this distance is limited and based on maximum interpupillary distance (IPD) of a human's eye, while with a 3DAMD microscope one can adjust the system irrespective of IPD and apply a greater physical distance between the sensors and/or apply disparity 3D imaging algorithms, which makes for better quality 3D. In addition, a SOM requires the user to have a limited, single field-of-view at high zoom, meaning that the context tends to be lost, while with a digital microscope, you can have a picture-in-picture or picture-in-picture which references where you are in the larger structure to be viewed at higher zoom.

Even though some SOM systems provide the advantage of offering an ocular only view or a digital view, or both, the result comes with limitations in the form of posture constraints, which typically forces the surgeon to unergonomic positions for hours of surgery use, often causing neck, back, hip, and hamstring strains. Many surgeons find they have to retire early due to such stress and strain or must undergo surgery themselves to alleviate work-related musculoskeletal disorders (WMSDs), which are prevalent among surgeons and often result in practice modification. Some medical investigations show that WMSD's exist in as much as 66% to 94% of surgeons practicing open surgeries, with surgeons showing 73% to 100% WMSD's for conventional laparoscopic surgeries, and a rate of 54% to 87% for vaginal surgeries, and 23% to 80% of WMSD's reported from surgeons involved in robotic-assisted surgery.

Risk factors for WMSD's include the use of loupes, headlamps, OM microscopes, and robotic-type assisted surgery systems that have control booths where the operating surgeon is totally divorced from the patient and surgery site. In the instance of the robotic systems, the surgeon is typically secluded in an enclosed console, which may or may not be in the same room with the patient. So, the surgeon typically must depend on the surgery techs, who are physically present with the patient, to tell the surgeon if the robotic arms are in conflict, or if there is an unexpected patient event, such as a bleed. In the case of an unexpected patient event, typically the surgeon is dependent on a technician to advise him of that occurrence, and then the surgeon has to have the techs raise the robotic arms, while the surgeon is scrubbing up to sterilize to render aid. With the AXR technology of the present invention, such remoteness of the surgeon is overcome.

Moreover, the huge space which is needed for the existing robotic and legacy surgery equipment may compromise the surgeon's ability to view digitally or have the space needed for positioning during surgery, with one report concluding that: "Future research must aim to develop objective surgical ergonomics instruments and guidelines and to correlate ergonomics assessments with pain and tissue-level damage in surgeons with WMSDs. Ergonomics training should be developed to protect surgeons from preventable, potentially career-altering injuries." (Catanzarite T, Tan-Kim J, Whitcomb E L, Menefee S. Ergonomics in Surgery: A Review. Female Pelvic Med Reconstr Surg. 2018 Jan./Feb.; 24(1): 1-12. doi: 10.1097/SPV.0000000000000456. PMID: 28914699.).

Thus, the legacy systems and their add-ons have not provided the OR personnel with the best state-of-the-art in digital 3D technologies and better ergonomics that are provided by employing the multi-option fully digital 3D cobotic surgical system as set out herein.

Others have attempted to employ virtual reality (VR) surgical or diagnostic headsets. However, a VR headset totally immerses the user into the images presented, essentially totally blocking and replacing the user's field of vision of the real-world, often called the real-reality (RR), with virtual images and the impossibility to see the virtual image and the RR around the OR personnel. Such systems are defined by their replacement of the reality around the user with a total virtual substitute. This immersion locks the surgeon into a virtual space that is not easy to extract from in case of an urgency or emergency. The invention viewing option disclosed following transverses these limitations.

Such existing virtual reality surgery systems are generally uncomfortable and must be worn tight on the head, blocking out reality. VR systems seal out real-word light, sound, and the air around the surgeon's eyes and cheeks, making the device hot and uncomfortable. The heat generated by the surgeon wearing the VR headset and from the headset itself often causes condensation on the interior lenses, which makes the images appear foggy and requires the surgeon to take of the VR headset for cleaning during the surgery. Clearing the lenses typically only helps temporarily. Some such systems use a trackpad that is turned 90 degrees from the user interface, so that swiping forward actually moves right and swiping backward moves left. This can be frustrating for the user, particularly if the user is left-handed. Moreover, typing within a VR headset menu is a painstaking and time-consuming chore, making entering HIPPA compliant passwords for sensitive data difficult. Furthermore, such virtual reality systems are typically heavy, with most of the weight forward on the head, making it uncomfortable for the user.

To address these concerns, augmented/extended reality (AXR) surgical systems have been introduced for surgical use. Whereas virtual reality immerses the user into the images presented and closes RR, AXR permits the surgeon, nurse, assistant, or tech user to see RR and what is actually happening in the user's world and then adds computer-generated, computer-manipulated, or secondary camera images to RR. Thus, while virtual reality completely covers and replaces the user's field-of-vision with virtual images, augmented/extended reality provides the user with vision of the real-world plus an overlay of computer-generated and/or manipulated photographic imagery or video ("virtual") images, which positions the user in the RR with virtual images added.

In an operating environment, an augmented/extended reality system permits the surgeon to both view and have magnified the virtual (streaming surgery) image or video of the operation site, while still having a visual sense of the operating or diagnostic room and being with all the other things happening in that space. The problem with current AXR surgical systems that typically rely on waveguide technologies or laser beam scanning plus waveguide technology is that they all offer a small field-of-view (FoV) and limited resolution and are typically waveguide or laser beam scanning technology combined with a waveguide. In addition, they typically are on a heavy wearable that is often tethered to the system by a large cord, limiting the surgeon's movements and putting strain on the surgeon's neck and back. Furthermore, current AXR surgical systems must block out a great deal of ambient light to make the AXR images visible and are difficult to see in daylight or highly-lighted conditions, making the systems function more like a virtual reality system than an AXR system, which erases the benefit of AXR.

Based on the foregoing, it is desirable to provide a true AXR surgery system that provides a plurality of potential video or image feeds or overlays of computer-generated images while maintaining a sufficient real-world view. Specifically, it is desirable to not use waveguide technologies but, rather use an AXR headset which is a wearable pupil-forming display apparatus, comprised of two axially symmetric pupil expanding ocular engine with a folded prism so that the micro-displays, which are the warmest electronic in the headset, are the furthers away from the wearer's head and body.

It is further desirable for the AXR headset be lightweight, comfortable, untethered, and is feature- and user-friendly.

It is further desirable for the AXR headset to offer a wide FOV and high resolution, which is not currently possible with AR waveguide technology or laser beam scanning technologies combined with waveguides. Thus, in the preferred embodiment, the AXR headset may have it optical engine based on near-eye pupil forming catadioptric optical engine, which provides a wide field-of-view and pixel accurate photo-realistic imaging. By using this system with OLED micro-displays, it is easy to adapt this type of optical engine when the next level of imagers, the micro-LED engines to come out in the future. The near-eye pupil forming catadioptric optical engine may be designed with a bird-bath design so that new display technologies are adapted by OLED replacement LED plug and play technologies.

While the focus of this invention is on its application to the medical and surgical fields, it is further desirable for the same techniques to be utilized in other sectors while wearing a lightweight, comfortable, untethered, feature- and user-friendly AXR headset would be of benefit.

Further, the surgery visualization system presented herein may provide other viewing options besides the AXR wireless headset, such as (i) an autostereoscopic monitor featuring lenticular lenses or parallax barrier which does not need polarized 3D glasses for the user to view the surgery image in 3D, which may be mounted on a cobotic arm; (ii) a 3D digital viewport (3DDV) device, which may be mounted on a cobotic arm which may traverse to advance to the OR personnel and then, through sensor technologies, moves with user as his or her posture changes or slouches during surgery. Some of the sensor technologies which may be employed are SLAM technologies, facial-recognition technologies, head-tracking, eye-tracking technologies, and time of flight technologies. The one or more 3D viewing options may be provided in the first instance by a new type of 3D all-digital stereo microscope (3DADM) which may feature two full-frame 35 mm or higher 4K, 6K, or higher resolution sensors with large pixel size of 5 microns or more, providing as much as 69 billion possible colors, which is more than the human eye can distinguish, which also may be mounted on a cobotic arm. The surgery visualization theatre may also comprise at least one computer and graphics unit, together with multiple methods of transmission including wire connected transmission; or any of the existing wireless transmission technologies. The surgery visualization theatre may also comprise a model controller to control the components and the digital microscope and viewing options to keep them in sync with each other.

SUMMARY OF THE INVENTION

In general, in a first aspect, the invention relates to an all-digital multi-option 3D viewing theatre (ADMO3DV). The surgery visualization theatre may offer multiple options for viewing a surgery feed in 3D comprising: an augmented/extended reality (AXR) headset which may be preferably connected wirelessly to the theatre, but may alternatively be wired; a 3D digital viewport, which may be mounted on a cobotic arm; an autostereoscopic monitor, which may be mounted on a monitor cobotic arm; a camera microscope subsystem, which may be mounted on a camera cobotic arm; and a frame, where the microscope cobotic arm, the monitor cobotic arm, and the camera cobotic arm are mounted on the frame. The frame may cantilever over the gurney and use any of hydraulic, pneumatic, electronic actuator, springs, or band to control the movement of the cobotic arms, which may be 6 axes more or less. The cobotic arms may be cartesian, SCARA, cylindrical, delta, polar, or vertically articulated or other robotic mechanism.

The AXR headset may have two micro-displays and each of the two micro-displays may have a resolution of at least 4K. The micro-displays may be capable of active pixel phase shift. The 3D digital viewport may have two micro-displays and each of the two micro-displays may have a resolution of at least 4K. The 3D digital viewport's micro-displays may be capable of active pixel phase shift. The 3D digital viewport mounted on the cobotic arm may be a six-axis more or less cobotic arms. The monitor may be a 3D autostereoscopic glasses-free monitor, meaning that no 3D glasses need be worn by the viewer(s), capable of providing, in the best embodiment, at least 4K resolution to each eye of a user.

The 3DADM subsystem may comprise two 4K 6K, 8K, or higher resolution cameras and a light source.

The monitor cobotic arm and/or the camera cobotic arm may be any type of robotic arm described herein. The frame may be capable of swiveling and reversing for right or left-handed use.

The surgery visualization theatre may further comprise and include a 3DDV with embedded SLAM technology and a plurality of sensors such that the system is capable of moving the 3DDV oculars on the cobotic arm to position the digital viewport in front of a user's face upon a cue by the user and then through the use of SLAM, time-of-flight (ToF), depth estimation from stereo cameras, a combination of ultrasonic sensors with single camera face tracking, to keep the digital viewport always moving in alignment with the surgeon as he moves, slouches, or adjust during a surgery. The digital viewport cobotic arm, the monitor cobotic arm, and/or the camera cobotic arm may use a low-friction, gravity compensated controller The digital viewport may comprise one or more eye cups or oculars for the user to place his eyes against, essentially like a surgeon would do to view images with a SOM, except that the surgeon would be, in this instance, looking at micro-displays projecting the surgery image or video feed to his eyes. In addition, the digital viewport may have an automatic or manual adjustment for interpupillary distance (IPD) so that when viewed with two eyes in both oculars the image presented is a 3D image.

The AXR headset may be capable of protecting a user's eyes while in the vicinity of medical lasers with either a film or liquid crystal layer on the exterior of the AXR headset, which may be comprised of a collector lens and an additional external lens which contains the film or liquid crystals. The AXR headset may further comprise a clip-on face mask, which may be an N1 filtration capability mask and/or use photocatalytic (UV energized titanium dioxide coated surface) active pathogen oxidation techniques. The clip-on face mask may be capable of using a combination of photocatalytic pathogen oxidization and post filtration to capture any spuriously created ozone before inhalation.

The 3DADM may contain a lens magnification and focusing system, and dual sensors for 3D viewing, software, algorithms, and processing capability, including a model controller, computer vision technologies, and computer graphics technologies. Hardware may include a series of lens beginning with an objective lens, which both camera channels share, from there the dual optical channels may magnify a certain specified amount in tandem, including optical zoom. The sensors may be the end of the optical engine and receive the information for processing and sending for viewing. In one embodiment, the sensors may be rotated on the aperture azimuth for viewing at multiple azimuth degrees. The 3DADM may contain internal lighting or can be used with external lighting like which is used in vitreoretinal surgeries.

Figure 1:
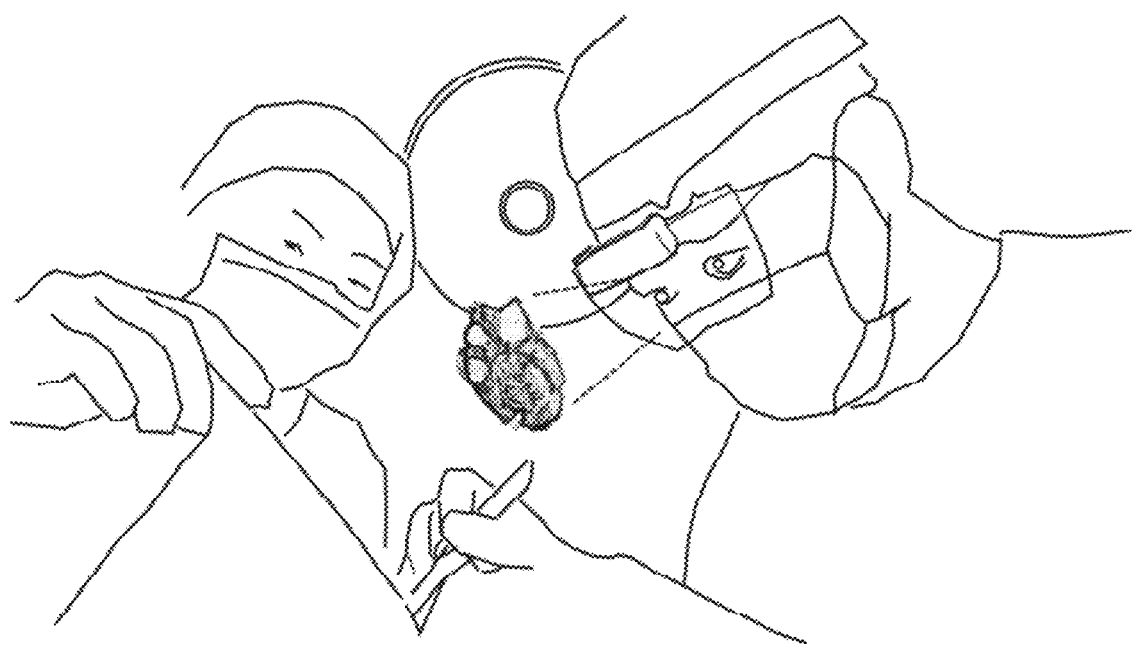
FIG. 1 is a perspective view of the AXR surgical system in use.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

"Augmented and Extended Reality" (AXR) is defined herein in its common scientific use, which may include an interactive experience typically in a see-through headset with lenses of a real-world environment where the objects that reside in the real world are enhanced by computer-generated perceptual images and information, sometimes across multiple sensory modalities, including visual, auditory, haptic technologies, somatosensory, and/or olfactory.

"Extended Reality" is defined in its common scientific use, which is typically an umbrella term encapsulating augmented reality (AR) and/or virtual reality (VR) and/or mixed reality (MR) and/or real reality (RR) and everything in between. It may also include combined environments and human-machine interactions generated by computer technology such as 6DoF and SLAM, and artificial intelligence (AI), including machine learning (ML), where the 'X' represents a variable for any current or future spatial computing technologies, including digital content of any sort; for instance, in the medical field, a 3D MRI or CT scan images or data visualizations, like patient vitals, superimposed or overlaid on an AXR headset in one of the several methods outlined herein.

"Artificial Intelligence" (AI), sometimes called "Machine Learning" (ML), is used herein in its common scientific meaning, including referring to the simulation of human intelligence in machines that are programmed to think like humans and mimic their actions and decisions. The term may also be applied to an augmented reality headset that exhibits traits associated with a human mind, such as learning and/or problem-solving. AI may enable AR to interact with the physical environment in a multidimensional way. For instance, AI may permit object recognition and tracking, gestural input, eye-tracking, and voice command recognition to combine to let the user manipulate 2D and 3D objects in virtual space with the user's hands, eyes, and/or words.

"Cobotic" is used herein in its common scientific meaning, including a robotic function which is pre-programed and automatic, and human control, which augments the pre-programmed function. For instance, a cobotic arm could be set from "repose" position to fully extend, however the extension is augmented and guided by one or more of facial recognition, eye-tracking, head-tracking, hand gesturing technology, verbal command, manual command, time-of-flight, dept perception, SLAM and Object Recognition, and 6D0F (the cobotic arm knows where it exists in the world). It can operate on a relative coordinate system that tells it where to go; where to be stored on "repose"; and directs its travel to the user's preferred use position, based on user preference settings. However, a user can manually take control, which shuts off the end-point of the automatic control, and it responds to the manual placement by the user. Then, as the user begins to re-position, slumps, or adjusts, the cobotic arm carries the 3DDV instrument with the re-adjustment of the user position so that good ergonomics are always maintained. As used herein, cobotic is a term describing an articulating or robotic action arm of the appropriate length and joints of appropriate load bearing with the added dimension of the ability for human touch, voice, or other control to interrupt and re-control the pre-programmed robotic functions. As used herein, the cobotic arms may be a type of articulating arm robot, or a Cartesian coordinate robot arm, also called linear robot, whose three principal axes of control are linear, i.e. they move in a straight line rather than rotate, or a selective compliance assembly robot arm or selective compliance articulated robot arm (SCARA) robotic arm with parallel-axis joint layout, the arm is slightly compliant in the X-Y direction but rigid in the 'Z' direction, hence the term: selective compliant, or any other type of mechanical programmable arm, with similar functions to a human arm; the arm may be the sum total of the mechanism or may be part of a more complex robot or the surgery visualization theatre herein.

The term "image(s)" or "virtual image(s) or "imaging" or "virtual objects" or "AXR imaging" is defined for the purpose of this patent as visualization of either 2D images or video or 3D images or video. The definition also includes the concept that one or more 2D images can be viewed in stereoscopy to create one or more virtual 3D perspectives. Further included in the "image(s)" definition, herein, is the idea that AXR 3D models may be viewed as a single or series of 2D images, as in a still picture or video, or a single or series of stereoscopic 3D images, as in a 3D images or video. The 3D effect may be created in the AXR headset by using an off-set paired perspective of a 3D model. In addition, 3D models in AXR can be viewed from different perspectives by the user or multiple users can view the same image from multiple perspectives.

The term "wireless" as used herein means the electromagnetic transfer of information between two or more points which are not connected by an electrical conductor, or a communication by technologies, such as light, magnetic, or electric fields, or the use of sound. The term "wired" communication as used herein includes all methods of wireline communication including, but not limited to, directly connected devices, telephone networks, ethernet connections, cable networks, internet access, fiber-optic communications, and waveguide (electromagnetism) connections.

The following are sensing and control technologies which may be utilized by the ADMO3DV system:

"Six Degrees of Freedom" (6D0F) is defined herein in its common meaning, including the way virtual objects can be moved in virtual space in AR. There are six total degrees of freedom in placing virtual images in AR. Three (3) correspond to rotational movement around the x, y, and z axes, commonly termed pitch, yaw, and roll. The other three (3) correspond to translational movement along those axes, which can be thought of as moving forward or backward, moving left or right, and moving up or down.

"Inertial Measurement Units" is used herein in its common scientific meaning, including referencing devices for measuring rotational movements, such as an accelerometer, a gyroscope, and a magnetometer, all located within the AXR headset. These IMUs may measure the headset's velocity, orientation, and gravitational forces to infer rotational orientation and movement.

"Haptic technologies" is used herein in its common scientific meaning and is sometimes called kinaesthetic communication or 3D touch. It may also refer to any technology which may create an experience of touch by applying forces, vibrations, or motions to the user or to an object. Haptics may enable users to feel the sense of touch via vibrations of forced motion. Haptic technologies can be used to create virtual objects in a computer simulation or virtual space, or to control those virtual objects, and may be used to enhance remote control of machines and devices (telerobotics). Haptic devices may incorporate tactile sensors that measure forces exerted by the user on the interface. This technology may employ touch sensors for control.

"Object Recognition" (OR) or "Object Identification" (O1) is used herein in its common scientific meaning, including a computer vision technique for identifying objects in images or videos. Object recognition may be a key output of deep learning and AI algorithms. When humans look at a photograph or watch a video, we can readily spot people, objects, scenes, and visual details. OR/OI does this from visual analysis based on a neural network algorithms reconciliation with pre-existing information.

"Simultaneous Localization and Mapping" (SLAM) is used herein in its common scientific meaning, including a technology that understands the physical world through a 3D grid of feature points. SLAM maps what the camera and sensors see in three dimensions with correct spatial information and distancing. This may make it possible for AXR applications to recognize RR 3D objects and scenes, as well as to instantly track motion in the RR, and to overlay digital interactive augmentations. SLAM incorporates the application of sensors sensing dept, time-of-flight, and creating a 3D grid. SLAM also incorporates infrared sensing and measurements.

The following terms relate to the virtual/augmented images on the AXR headset:

The term "lux" is the SI derived unit of illuminance and luminous emittance, measuring luminous flux per unit area. It is equal to one lumen per square meter.

The term "lumen" is the SI derived unit of luminous flux, a measure of the total quantity of visible light emitted by a source per unit of time.

The term "luminance" is a photometric measure of the luminous intensity per unit area of light traveling in a given direction. It describes the amount of light that passes through, is emitted from, or is reflected from a particular area, and falls within a given solid angle.

The term "candela" is the SI unit of luminous intensity. The candela per square meter is the derived SI unit of luminance. It is from the candela that we get the modem measurement of NIT, which is commonly referenced in wearable and cellular applications. The term "NIT" is a non-SI name also used for the candela per square meter. As a measure of light emitted per unit area, this unit is frequently used to specify the brightness of a cellular or wearable display device. The sRGB spec for monitors targets 80 cd/m2. Typically, calibrated monitors should have a brightness of 120 cd/m2. As system described herein uses a NIT reference for its light/brightness measurements.

The all-Digital Multi-Option 3D Viewing Theatre.

Figure 22:
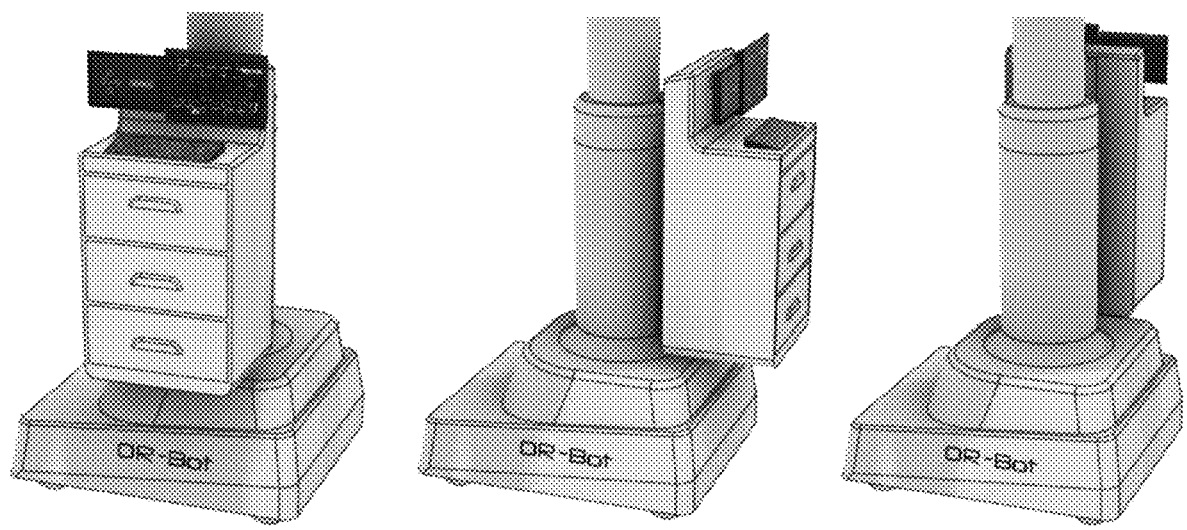
FIG. 22 is a series of perspective views of the cabinet and drawer system.

The ADMO3DV 100 system may have one or more connected viewports in addition to multiple connected AXR headsets, which may derive a surgery feed from the 3DADM 102. The connected viewports may include one or more of a 3DAM 104 and a 3DDV 106. The ADMO3DV may be a non-invasive robotic arm system with a large electronic actuator lift in the form of a cylinder mounted on a smart pedestal 108 on which is hung a translating top to hold a balanced cobotic arm system. The system may have a cabinet and drawer system 110, as shown in FIG. 22, and may contain the main computer, control, and wired and wireless connection/transmission system. The system may have its own keyboard and monitor for inputting settings, connecting with other OR equipment, and inputting or outputting EMR an imaging. The non-transitory model view controller (MVC) may synchronize the subsystems and may control all input and output according to the software programs. It may also house and control all the subsystems, including the AXR headset and cobotic arms with their viewing options as well as the 3DADM microscope. An operator may input the appropriate settings and model the control system may utilize keyboard, Bluetooth, voice control, eye-tracking, or gesture recognition or other technologies identified herein, and may also utilize SLAM and 6D0F technologies to operate properly wirelessly or use any other sensing and control technique stated above. Alternatively, one or more of these technologies may be used together in order to access and manipulate a control of the viewing system or microscope system attached to the cobotic arms. This method may allow the user to control the AXR system, autostereoscopic 3D monitor, 3DDV, 3D microscope, or other external equipment or systems via wired or wireless connection without requiring input through foot pedals, buttons, hand dials, or other hardwired methods of control. Combining two or more methods of control, i.e., voice with eye-tracking, may provide redundancy and ensure proper operation of controls.

The ASMO3DV system may provide an enhancement to existing surgery systems in several ways. First, as time is money, a surgery team does not have to re-position the typical 3D television monitor as the cobotic arms move the monitor to the exact position needed by the OR healthcare provider, based on the sensing and control technologies outlines herein.

The AXR 3D Headset Technology.

Figure 23:
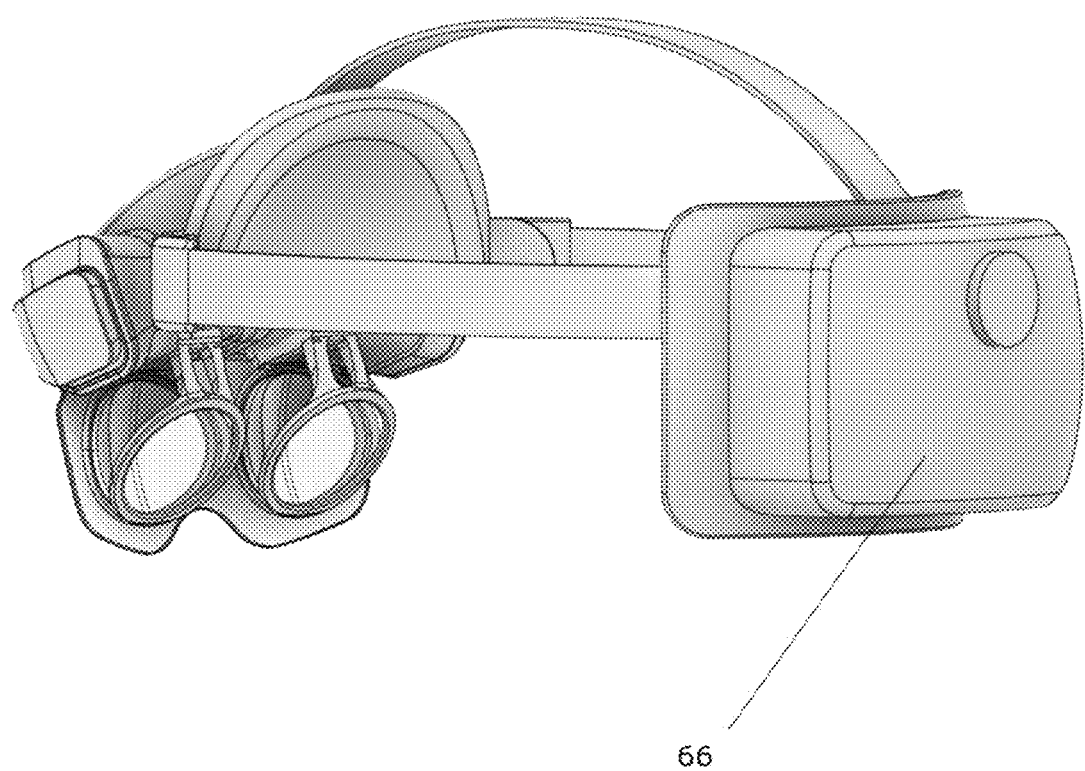
FIG. 23 is a back perspective view of the AXR headset with a larger battery box.
Figure 24:
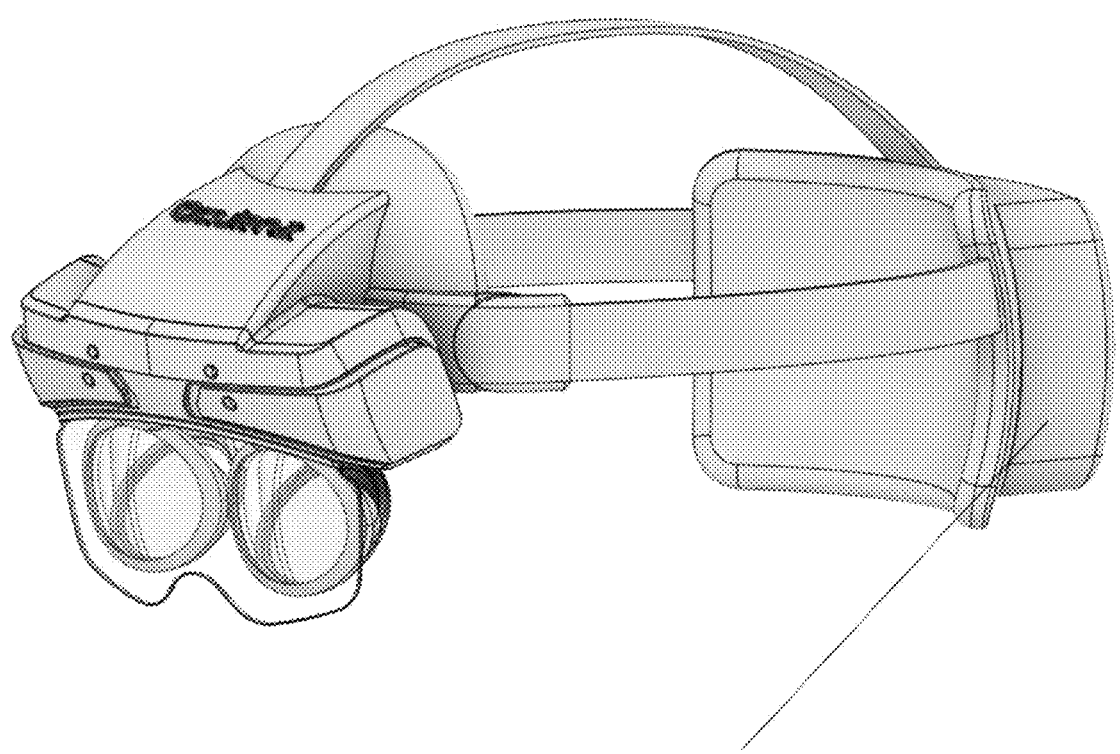
FIG. 24 is a front perspective view of the AXR headset with the larger battery box.

In general, in a first aspect, the ADMO3DV system invention relates to an augmented and extended reality (AXR) surgical system option which can be either wired or typically the preferred wireless headset. The system may comprise a wearable device 1, such as a head mounted display (HMD) or glasses, that provides the user with virtual reality (VR), augmented reality (AR), and/or mixed-extended reality (XR) for surgery visualization, as shown in FIG. 1. Alternately, it may comprise a system as shown in FIG. 23 with a larger battery box 66 for longer surgeries. This may allow the user to access 2D or 3D imaging, magnification, virtual visualization, six-degrees of freedom (6DoF) image and simultaneous localization and mapping (SLAM) management, and/or other images while still viewing real reality (RR) and thus maintaining a presence in the operating room. The AXR headset control of the virtual world may include sensors including haptic sensors which may be worn on the hands and connected to the headset for coordinated control.

Figure 2:
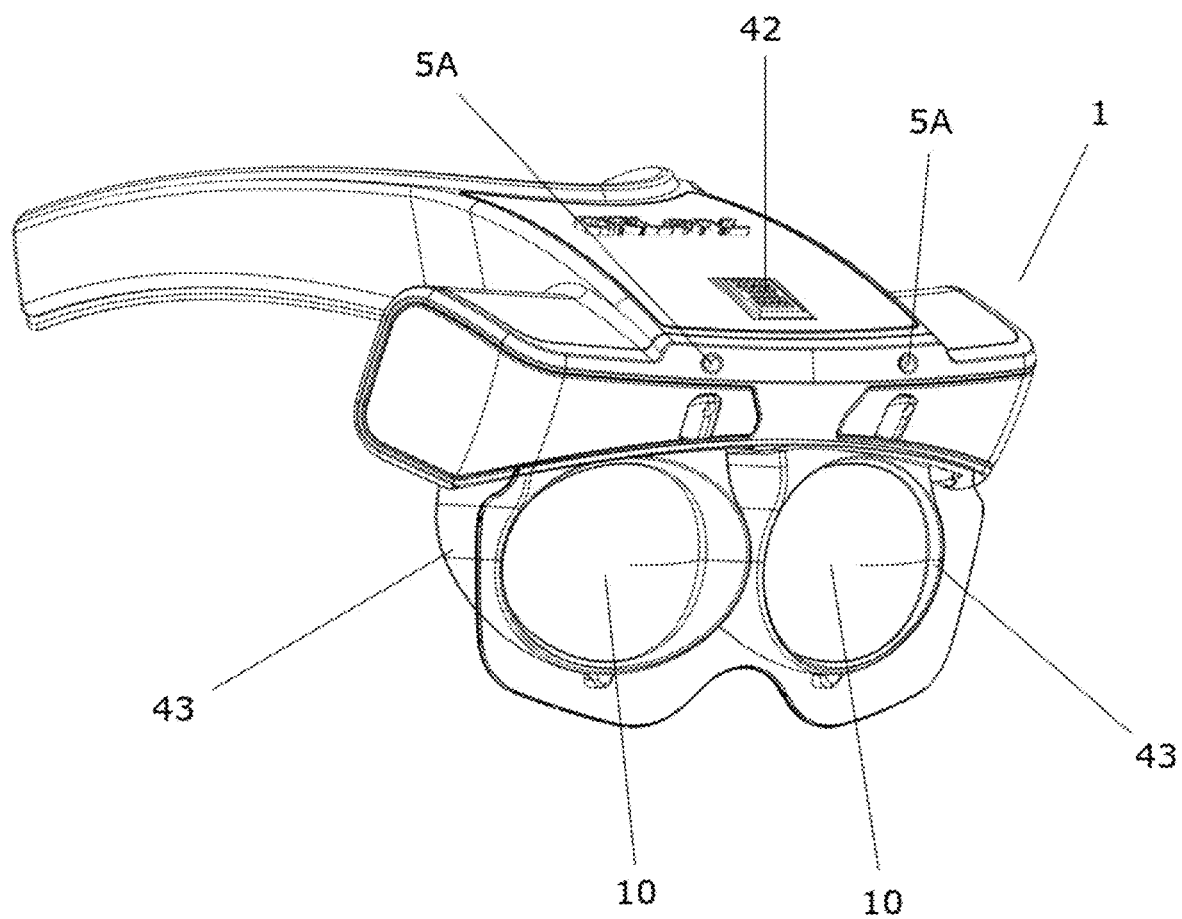
FIG. 2 is a perspective view of the AXR surgical system headset.
Figure 3:
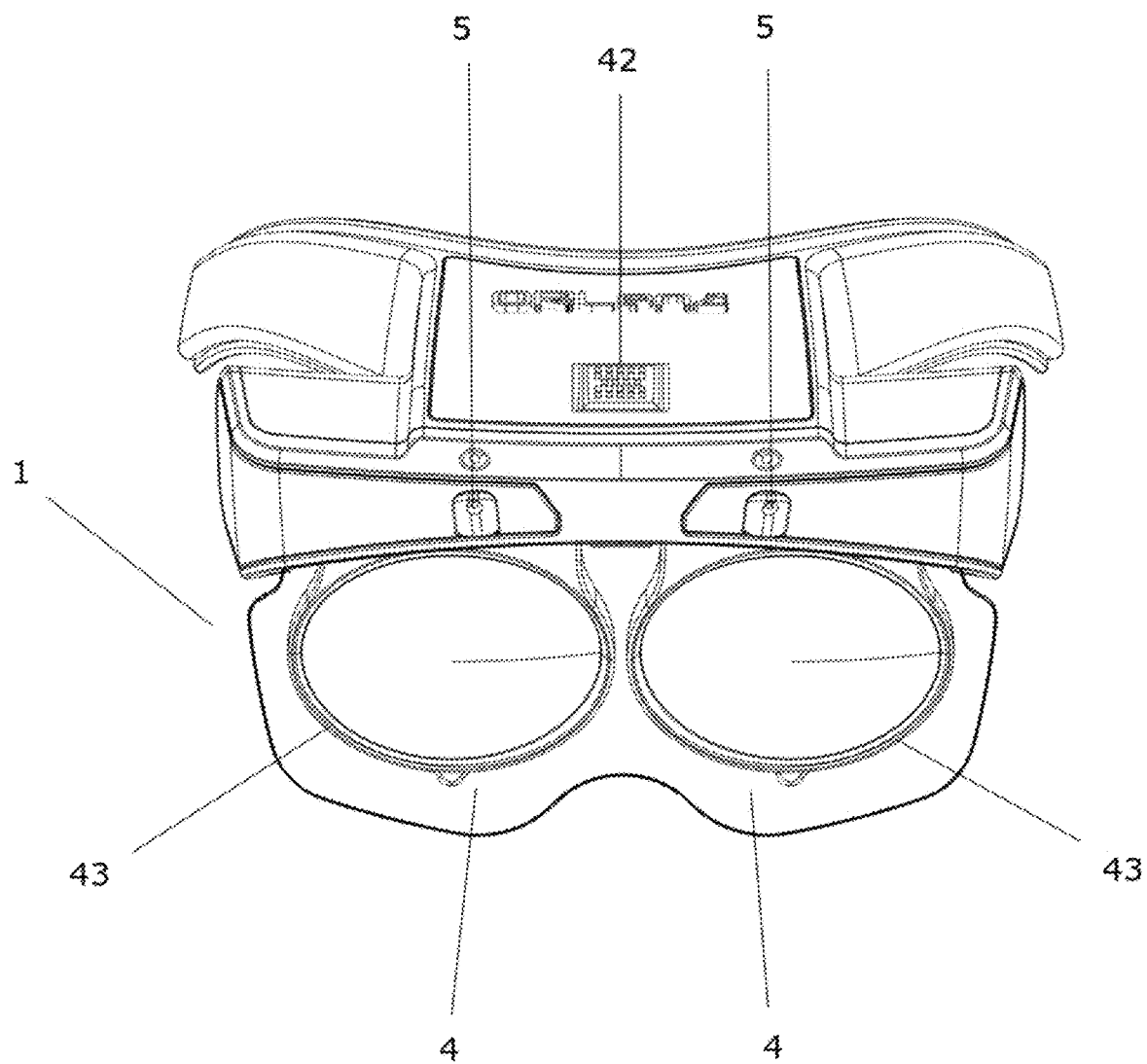
FIG. 3 is a front view of the AXR surgical system headset.

The AXR headset system may comprise one or more micro-displays 2, a head-tracking subsystem 3, an eye-tracking subsystem 4, and one or more cameras 5, all of which may be included on the wearable device 1. The system may further comprise one or more lenses 10, where the micro-displays 2 are capable of projecting images on the lenses 10, where the images may be reflected back to the user's eyes. For example, as shown in FIGS. 2 and 3, the wearable device 1 may be a head mounted display with a pair of lenses 10, one in front of each of the user's eyes. One or more micro-displays 2 may be located above the user's eyes and may be pointed toward the lenses 10. The two or more AXR cameras 5 may be 4K or higher each and may provide image input, while the head-tracking subsystem 3 and the eye-tracking subsystem 4 may provide positional input, allowing the system to project the desired images to the desired location for the user to view the images. In addition, the cameras may articulate to rotate downward to a position which may be 90 degrees from the plane of the front of the AXR headset. In this fashion, instead of a surgeon wearing loops, which causes the surgeon to put his chin on his chest throughout the surgery, the AXR cameras tilt and to the surgery site, leaving the surgeon with a more ergonomic and comfortable posture. Additional image input may be provided from other sources such as SLAM or other sensing cameras 5A. The AXR may be connected to the system and the 3DADM and my receive and transmit to the system for surgery visualization and commands back to the system.

All components may be controlled by a CPU and enabled by a GPU and one or more digital signal processors, cables, and battery source, which may be located on the wearable device 1 or remotely. Other components may include additional central processing units, one or more graphics processing units, one or more digital signal processors, firmware, hardware, software, and/or memory components, as well as other desired components, including a non-transitory model view controller. The high-level components may control the features and functions of the AXR headset 1, including, but not limited to, its cameras 5, micro-displays 2, lenses 10, sensors, communications, and subsystems.

Among virtual image display solutions for AXR viewing are catadioptric optics which are preferred in that they employ a partially transmissive curved mirror for directing image-bearing light to the viewer's eye and a partially reflective beam splitter for combining light generated at a 2D display with the real-world visible scene, which forms a superior 3D image and holographic images when viewed binocularly.

The headset may be wireless or wired. If wireless, the wireless module antenna may be connected to the main circuit board inside the headset and may radiate RF to the outside world through the WiFi, cellular, or 5G antennae 42.

The AXR headset may contain a small worm gear or similar device connected to the two lens frames 43, which may move closer and farther, approximately 5 mm, in order to adjust for interpupillary distance (TPD) for each person. This may be accomplished by the worm gear being connected to a spindle gear threaded on both ends, which may connect to the lens frames, which may be on a track that permits them this measure of movement. A remote Bluetooth connection may be housed in the charging station drawers, where it can automatically adjust based on the information preprogrammed into the ADMO3DV controller according to each user's IPD or can be accomplished manually through a small Bluetooth handheld device housed in each drawer and independently connected and secured to each device.

Figure 7:
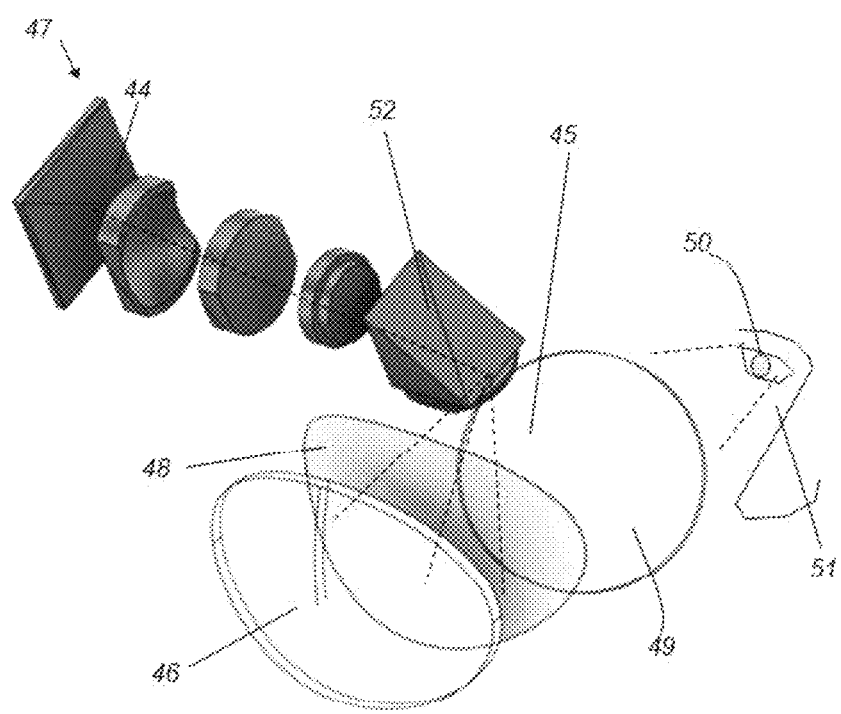
FIG. 7 is a break-out of the near-eye pupil-forming catadioptric optical engine in the AXR headset.

One such AXR headset, as shown in FIG. 7 and which may produce the best results for surgery, is an axially symmetric near-eye pupil-forming wearable AXR display apparatus comprising:

(i) relay of the image generator 44 to form a curved intermediate image 45 as a conjugate image. As a type of "aerial" image, intermediate image 45 may be formed in air, serving as the optical "object" for forming the virtual image. Intermediate image 45 may be formed along the curved focal surface of curved mirror 46, with the approximate aerial position shown by a dashed line in FIG. 7.

(ii) an optical relay 47, with particular structure as described in more detail subsequently, may conjugate the image formed from image generator 44 to the curved intermediate image 45 along the focal surface.

(iii) a curved mirror 46 may be partially transmissive, such as between about 30% to 70% transmissive, for example, allowing visibility of the real-world object scene to the viewer. A nominal transmission range of 50 to 70% may be useful in many applications and the see-through may be increased with the use of brighter imaging source such as an LCD or other micro display.

(iv) a beam splitter 49 may be used to reflect light from the relay 47 to the curved mirror 46 and may be an unpolarized or polarized beam splitter. It may transmit light from both the real reality external to the viewer and the virtual reality reflected off the surface of curved lens 46.

(v) use of a cylindrically curved quarter-wave plate (QWP) between mirror 48 and beam splitter 49. Curvature of this element may help to reduce variations of the retardation imparted to the image-bearing light by the QWP over the field of view.

(vi) large exit pupil 50. System optics can form a 10 mm exit pupil at the viewer's eye-box for eye 51. Forming a suitably sized pupil for the viewer may help to provide an eye box of reasonable dimensions to allow eye movement, without noticeable vignetting. Also, an enlarged eye box may permit the headset to move or slip without noticeable degradation of the viewed image(s). The apparatus may not need to provide pupil expansion, such as is used in existing wearable display apparatus, but may use pupil-forming optics for improved efficiency and brightness, as well as for improved image resolution.

Significantly, the eyes of the viewer may clearly see and be seen by others, with minimal impediment from the beam splitter and curved mirror optics that provide the electronically generated virtual image.

With the optical arrangement shown, the aperture stop AS may lie within prism 52 of the image relay, along or near the fold surface that is provided. This arrangement may be advantageous for component packaging and spacing, allowing the prism to be reduced in size over other configurations using a folding prism.

The given design may allow an FOV along the horizontal (x) axis, the axis parallel to a line between left and right pupils of the viewer's eyes, of greater than 50 degrees. The FOV aspect ratio (horizontal:vertical) may equal or exceeds 1.5. Digital correction may not be needed for distortion or lateral color.

According to an embodiment, curved reflector 46 may have a conic surface shape. The conic shape is advantaged, in the embodiment shown herein, helping to control chief ray angles, thus correcting for distortion. Depending on whether or not polarization is used for configuring light paths, beam splitter 49 can be either an unpolarized beam splitter or a polarizing beam splitter. Beam splitter 49 can be, for example, a wire grid polarization beam splitter as shown in FIG. 7.

Figure 5:
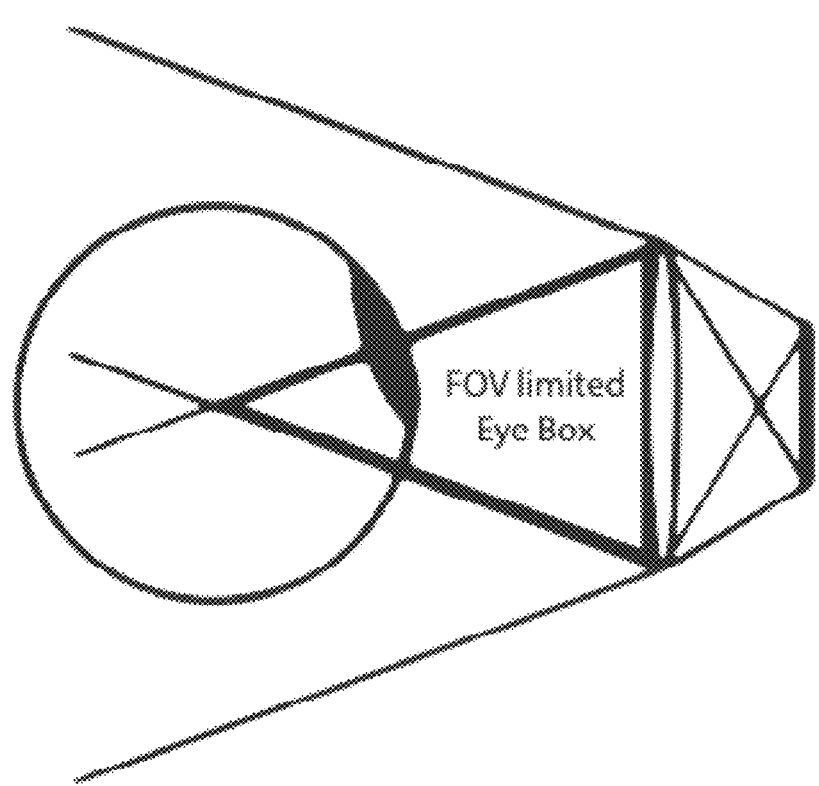
FIG. 5 is a diagrammatic illustration of an eye box.

The AXR system design may create a large eye box for the user, as shown in FIG. 5. The eye box of any AXR or VR system may be crucial as it may serve as the connection between the device and the user. The eye box of the system may be large enough to provide comfortable viewing of the full field of vision with the highest resolution and contrast even if the headset moves while wearing. Further, the eye relief of the system may be large enough to account for distance of the system to the user's eye, including allowances for brow size and how deep-set the user's eyes are, as well as clearance for eyeglasses. Thus, the near eye pupil forming catadioptric optical system as shown in FIG. 7 and described herein may be able to provide an image free of the type of chromatic aberrations typically found in a pupil expanding waveguide technology while maintaining a sufficient eyebox with good eye relief. The eye relief of a typical optical instrument is the distance from the last surface of an eyepiece within which the user's eye can obtain a full viewing angle. If a viewer's eye is outside this distance, a reduced field of view may be obtained. The eye box refers to the range of movement of the eye in which the system maintains an adequate image. Thus, the smaller eye box of previous VR systems is inferior to the large eye box of the current system.

Figure 6:
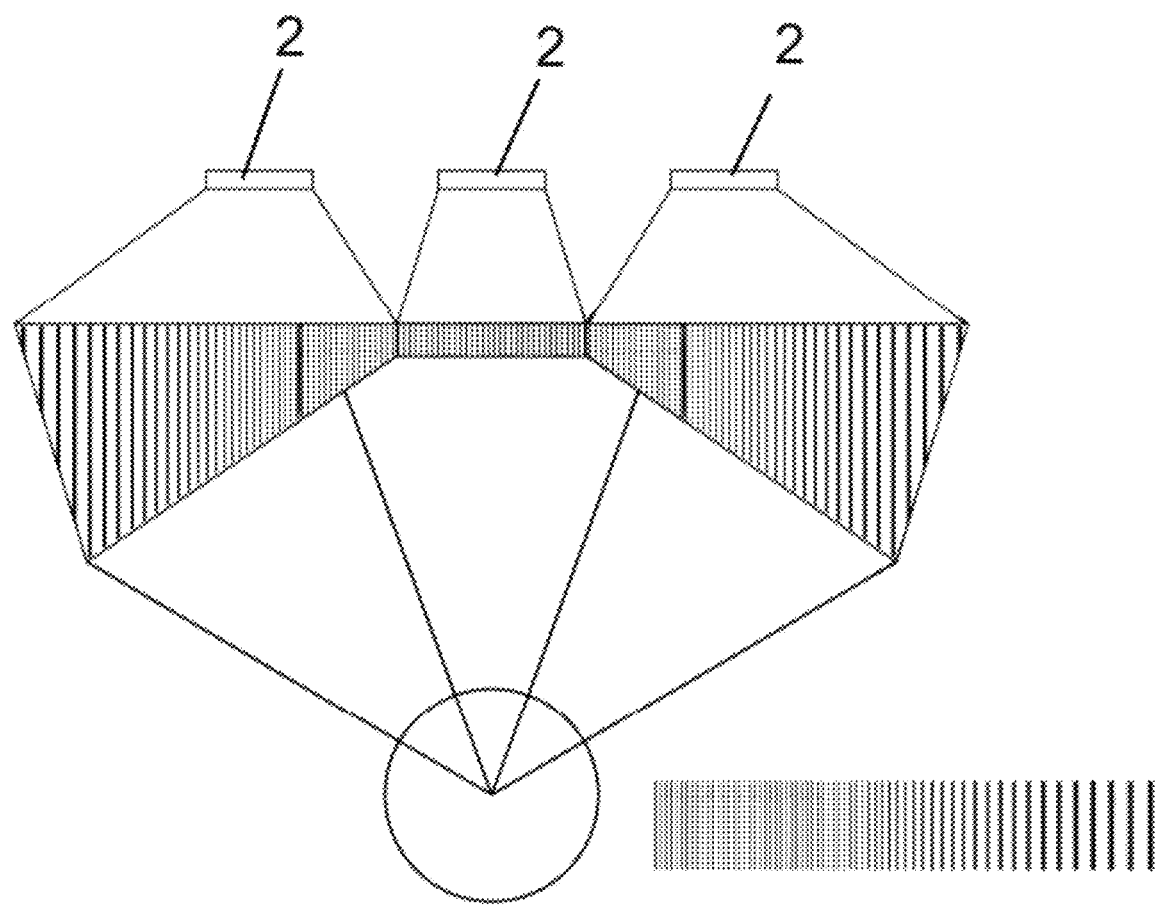
FIG. 6 is a diagrammatic view of the micro-displays.

Alternatively, an AXR headset may use a pupil expander mechanism, unlike the waveguide pupil expander, such as will create an eye box of as much as 20×20 mm×60p/p/d. This may be achieved by providing three micro-displays 2 having the outer two displays 2 sharing pixels with the central display 2 through the system's algorithms, as shown in FIG. 6. The system may present approximately 50 degrees horizontal by 20 degrees vertical field of view at 60 pixels per degree. The remainder of the field of view may have approximately 20 pixels per degree, which may be equal to or better than the acuity in the outer parts of the retina. The lenses 10 may be concave in construction, aiding to focus and enlarge the surgeon's eye pupil view for the biggest possible eye box. Thus, it is almost impossible for the user to lose the view of the AXR or surgery visualization image due to the large FOV and exceedingly high resolution of the system.

The AXR system may be capable of allowing the user's eye to rotate in order to view off axis field angles while still maintaining high resolution, either AR or RR, at approximately 50 pixels per degree. The optical engine in the system may accommodate not only large field of vision eye rotation, but also a translation of rotation of the pupil due to the fact that, in reality, the eye rotates about a point that is 10 mm behind the pupil, where the fovea actually exists. The optical engine may provide a virtually no-chromatic distortion display providing resolution of 56-60 pixels per degree. The optical engine may use an aspheric catadioptric off-axis engine. The asphere's more complex surface profile may reduce or eliminate spherical aberration and also reduce other optical aberrations such as astigmatism, compared to a simple lens. A single aspheric lens may be capable of replacing a much more complex multi-lens system when used in combination with an ellipse reflecting lens collector. The resulting device may be smaller, lighter, and less expensive than a multi-lens design. Aspheric elements may be used in the lenses to reduce aberrations, and in combination with reflective elements (catadioptric systems) such as the aspherical Schmidt corrector plate used in the Schmidt cameras and the Schmidt-Cassegrain telescopes or ellipse collector optical cut.

Features of the AXR optical engine may include micro-display lens correction, optical collimators in more than one place, reflective lens correction to adjust the focal point for near eye projection, dynamic opacity to compensate for brightness overcoming light loss, keystoning software distortion correction, IPD mechanical and/or software adjustment per person, and an off-axis, semi-spherical (elliptical) combiner in the inner portion of the lens.

The resolution of the AXR micro-displays 2 may specifically be 22 pixels per degree, or 2560×1440 (Quad HD); 25 pixels per degree, at 3200×1440; 60 pixels per degree at 7200×1600; or any other desired resolution. The luminance may be 1,000 cd/m2, or higher, while contrast may be 100,000:1 or higher. The micro-displays 2 may support 110 percent of the sRGB color gamut ratio.

Active pixel phase shift may be used to increase micro-display 2 resolution via timed spatial displacement. Resolution may be an important element for future uses of AR/VR glasses in critical use cases such as surgery visualization. In these scenarios, detail visualization of fine layer and blood vessels can be critical to successful outcomes. Today's current micro-displays are still maturing, and pixel counts of 2 million are common but higher resolution displays are still being developed and perfected. When higher resolution displays are developed, they may come with a steep cost to drive all those pixels. Using the following described elements may make higher resolution images available to users at a discounted power cost, which in turn may provide lighter, cooler running systems. The advantage may come in the ability to use a given number of pixels from an existing micro-display 2 multiple times, thus doubling or quadrupling the active resolution to the user. This multiplying of resolution may be accomplished by physically shifting the micro-display 2, for example, first horizontally U pixel, then vertically U pixel, then horizontally back to zero position, then vertically back to zero position, i.e., the original position. The power cost of nano scale piezo shifting may be much lower than the cost to design and implement four times the pixel count. The advantages of this system may include travel ranges from 100 µm to 600 µm; long device lifetime; high-precision, frictionless flexure guidance system; superior positioning resolution and linearity to 0.007% with direct-metrology capacitive sensor options; mounting compatibility with other QNP-series piezo nano positioners; and open-loop and vacuum versions. A variety of travel and feedback options can make a phase shift system like this an ideal solution for applications ranging from microscopy to optics alignment and provide a higher resolution than a native micro-display.

The micro-displays 2 may be organic light-emitting diodes (OLED or Organic LED), also known as organic electroluminescent (EL) diodes, which is a light-emitting diode in which the emissive electroluminescent layer is a film of organic compound that emits light in response to an electric current or LCD. This organic layer may be situated between two electrodes; typically, at least one of these electrodes is transparent. The micro-displays 2 of the system may each comprise a front plane and a semiconductor back plane manufactured by a silicone fab connecting the multiple front-plane screens.

Luminance is often used to characterize emissions or reflection from flat, diffuse surfaces. Luminance levels indicate how much luminous power could be detected by the human eye looking at a particular micro-display surface from a particular angle or view. Luminance is thus an indicator of how bright the surface will appear. In this case, the solid angle of interest is the solid angle subtended by the eye's pupil. Luminance is used in the video industry to characterize the brightness of displays. A typical computer display emits between 50 and 300 $cd/m^2$. The sun has a luminance of about $1.6 \times 10^9$ $cd/m^2$ at noon. Luminance is invariant in geometric optics. This means that for an ideal optical system, the luminance at the output is the same as the input luminance. The system of the present invention may have a midrange luminance.

For passive AXR optical systems, the output luminance is at most equal to the input. As an example, if one uses a lens to form an image that is smaller than the source object, the luminous power is concentrated into a smaller area, meaning that the illuminance is higher at the image. The light at the image plane, however, fills a larger solid angle so the luminance comes out to be the same assuming there is no loss at the lens. Thus, the image can never be brighter than the source. However, when a TV or video projector is touted as able to output 1,000 Nits or Lumens, that does not mean that the TV or projector outputs that much light all the time. Frames or scenes most often display a range of bright and dark content, as well as a variation of colors. All these variations require different levels of light output which is accounted for in the algorithms of the system.

The AXR micro-displays may be capable of emitting as much as 3,000 to 5,000 NITs per display, currently, with plans to enhance this brightness in the future. With two or three displays together, as in the alternative example above, the overall brightness may be increased across the viewing area.

When the micro-display emits 1,000 NITS, the eye-box value may be 300 to 500 NITS, depending on the image material. This may be adjustable by the user. For reference, a TV is designed for 300 to 500 NITS, but a computer monitor is designed at only 200 NITS because it is assumed that you will be looking at it for hours on end and the desire is to reduce eye strain.

Thus, in addition to considerations of brightness, one must consider the imposition of an electronic darkening of the entire lens or electronic darkening of just the area in which the virtual image is contained pixel by pixel. This idea has been called dynamic opacity, which, when added to the optical engine, may also provide additional brightness to the augmented reality image by electronically darkening the RR around or behind the virtual image. By making the real world (RR) behind the augmented reality (AR) image on a gradient from 1% to 100% opaque, the dynamic opacity may provide an even greater luminance referred to the eye.

Alternatively, a chemical photo lens may be used as the external lens which can turn darker by exposure to light independently from electronic activation. Such a light-responsive lens may begin to darken when exposed to UV rays in both direct and indirect light and then may fade back to clear indoors with the level of darkness and speed of transition depending on the level of UV exposure and temperature.

The AXR system may be capable of displaying both real reality and computer-generated images (CG or CGI) or computer captured and manipulated images (CMI), effectively creating the illusion of AXR. In this context, CMI may mean previously recorded, captured, or created images or video from a different reality than the RR displayed in the AXR headset. Additionally, or alternately, the system may be capable of functioning as a "heads-up" system, allowing the user to look at the images on the micro-displays 2 or look beyond the display to the larger environment of the real-world operating room and attendants. Thus, the AXR system may provide a full field of vision, unlike existing systems. Specifically, for example, the micro-displays 2 may provide a wide field of vision of, for instance, 120 degrees, namely 60 degrees horizontal and 36 degrees vertically or more degrees in each eye, or other desired field of vision. This may allow a high angular resolution of 60 pixels per degree in the eye box, which is the highest resolution the eye can distinguish at 20/20. Humans have a slightly over 210-degree forward-facing arc of their visual field. The cameras 5 of the system may capture all or most of the human forward-facing degrees, when needed. Correspondingly, the user may view 120 degrees field-of-view (FOV) of AXR through the AXR cameras 5 or the surgery feed from the 3D ADM and micro-displays 2 and 210 degrees of RR with the system functioning as a heads-up display (HUD). This field of vision may actually be even larger from a practical standpoint as the user may for example, look down at his or her hands, which are outside the AR/RR presented field of vision. The availability of viewing the RR environment may be important to a surgeon when he or she is trying to unfocus from the surgery site to a non-surgery site to pick up a tool or adjust his or her hands during surgery. This type of viewing is not possible with existing VR systems, which require the eye of the surgeon to be always exactly aligned, something that might well prove exhausting in a lengthy surgery.

The AXR cameras 5 may be two on-board 4K or higher resolution cameras and may as noted above, capture a wide field-of-view, such as 180 to 210 degrees forward-facing vision. This oversampling of the field of vision may then be stored per frame and used in conjunction with the eye-tracking subsystem 4 to present the actual field of vision depending on the user's gaze. In this fashion, the system may use images from the entirety of the 180 degrees captured or a reduced sample of the entire captured camera's FOV. The reduced sample may be based on eye-tracking and eye-gaze correspondently. As the system's eye-tracking follows the eye of the surgeon as his or her eyes move, the system may be able to provide a subset of imagery from the fully captured 200 or more degrees.

Figure 8:
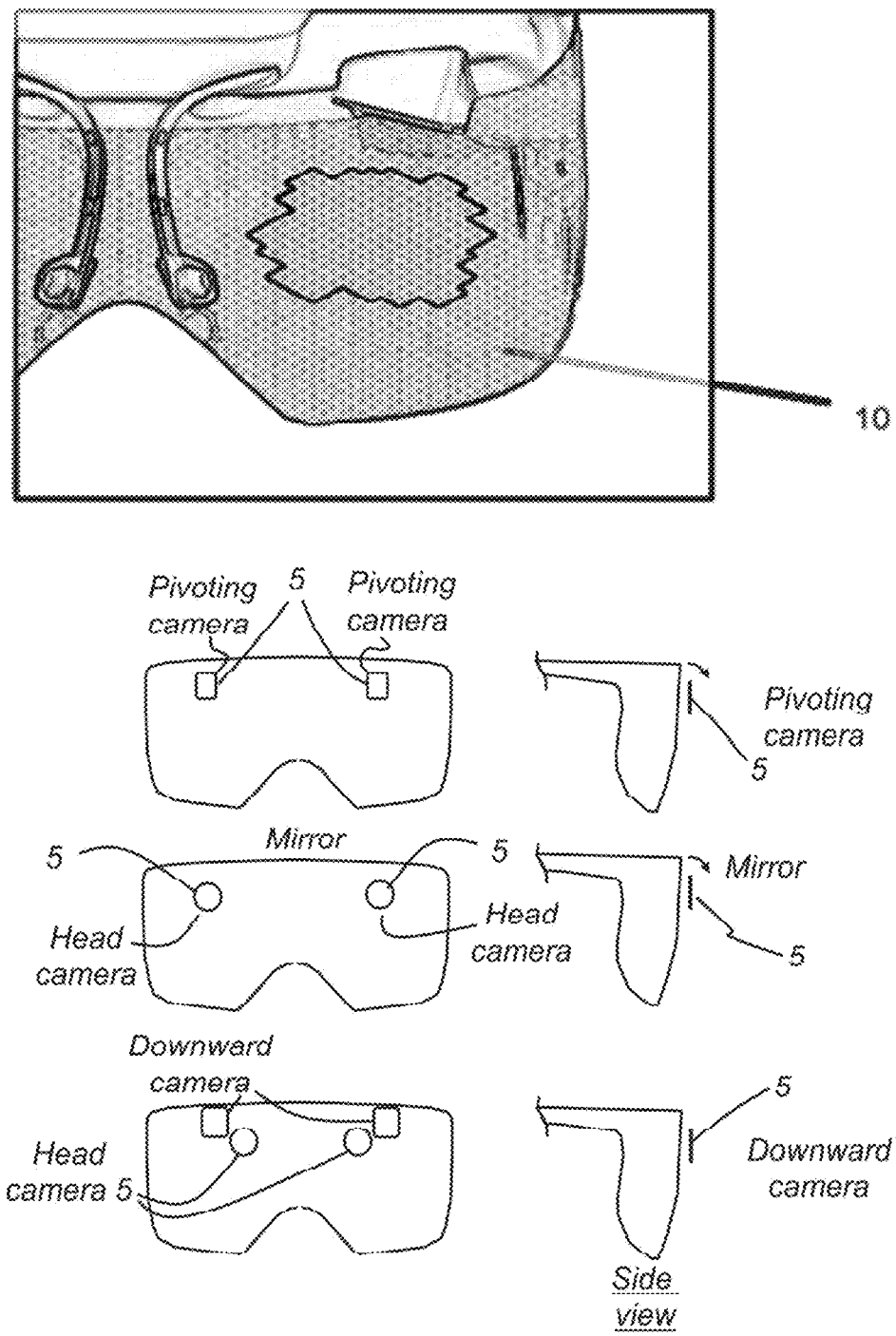
FIG. 8 is a close-up view of the dynamic opacity and the rotating articulation of the dual headset cameras up to 90 degrees.
Figure 9:
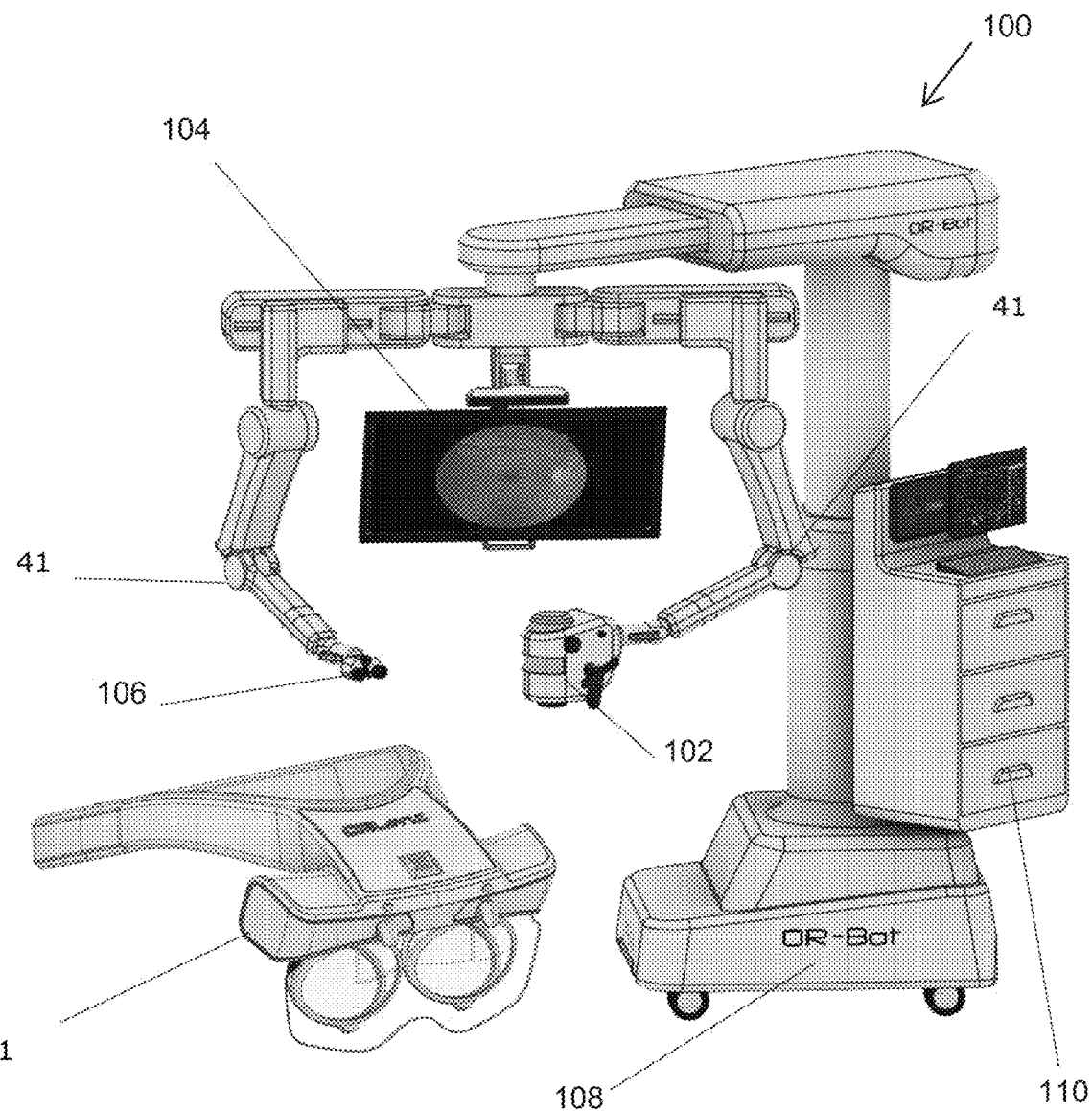
FIG. 9 is a view of the overall ADMO3DV surgery suite with its 3D microscope and three (3) 3D viewing options.

The two AXR headset cameras FIG. 8 may be rotated up to 90 degrees on axis by voice command or virtual menu, or other control mechanism, which permits a user to look straight ahead with an ergonomic posture, moving and adjusting as necessary, while the cameras pivot to show a surgery view of a patient on a gurney between 60 to 90 degrees.

Figure 12:
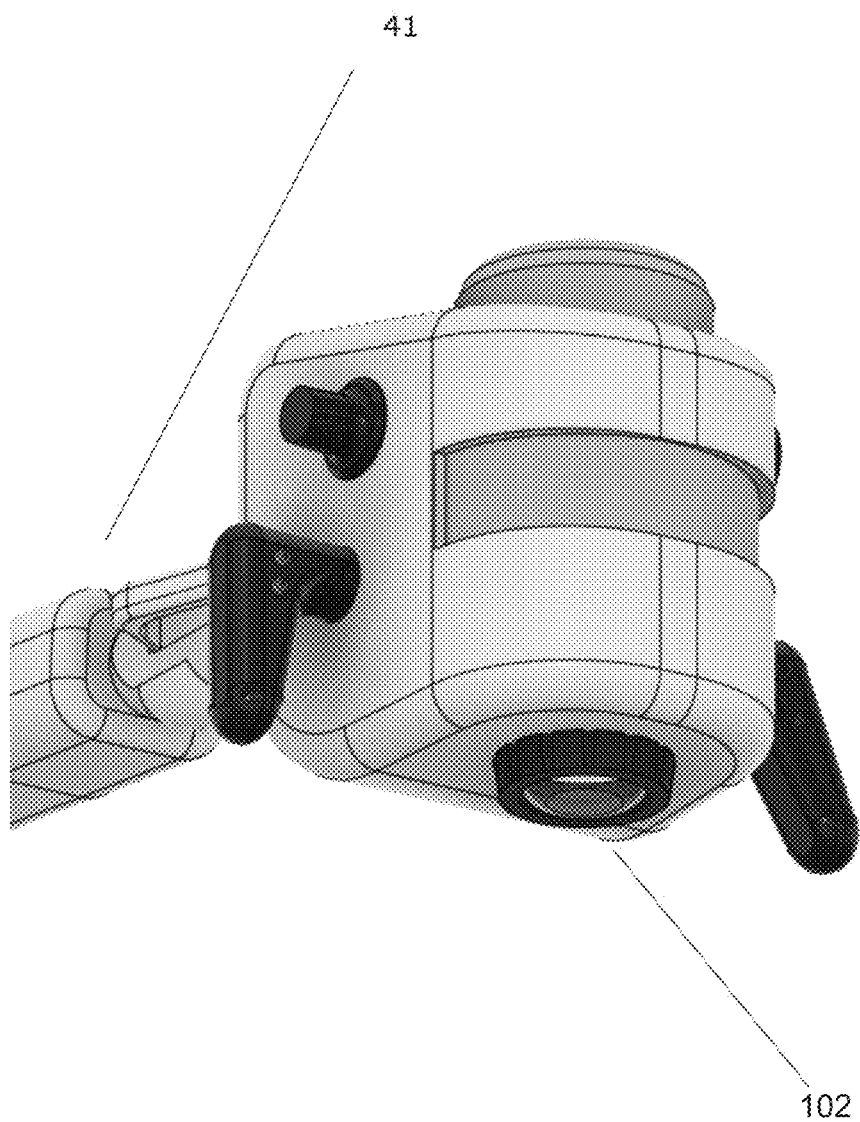
FIG. 12 is a diagrammatic view of the 3DADM dual camera sensor microscope with internal and external lighting options.

The AXR headset in combination with the 3DADM as shown in FIG. 12 with dual 4K sensors may provide up to 36 times zoom, 6 optical and 6 times digital zoom. The accelerometers, gyros, and magnetometers (IMUs) resident in the system's chipset may automatically enable and switch among the various video inputs depending on the position of the surgeons' head. When a surgeon looks down, the system may enable the front-facing cameras; when the surgeon looks up or straight ahead, the system may enable the downward cameras to permit the surgeon to comfortably find a looking-forward position where the downward-facing cameras capture the surgeon's hands and operating space. When a voice command is issued from the surgeon, the system may switch off the RR cameras and convert to projecting the images from a scope or digital microscope.

Alternatively, the virtual images projected by the microdisplays 2 may come from existing data, pictures, graphs, videos, MRI's, CT scans, or other pre-recorded images or information.

The one or more original source cameras may be mounted on the AXR headset 1 or may receive the surgery video feed connect to an external camera system like the 3DADM system described herein. Thus, the networked headsets and viewports of the ADMO3DV system may allow multiple participants to see and experience the same surgery or diagnostic view or provide an experienced surgeon with the ability to remotely assist an immediately present or remote inexperienced surgeon. This technique may be used to also teach and train healthcare workers. By continually monitoring and transmitting the image of a surgery between two or more distant users, the system may enable remote virtual telemedicine collaboration between multiple surgeons, assistants, techs, students, or others.

The system may optionally exactly align the CG or GMI image with the real environment in any of the viewports or the AXR headset. This alignment may be accomplished by creating an overlay, which permits the alignment of preoperative CT or MRI 3D images with the currently treated patient's body, body parts, or internal organs. In this fashion, while wearing the AXR headset 1, the surgeon may be able to both view the whole person in RR while seeing images of internal items like the person's internal organs, blood, bone, or tissue while using 6DoF, SLAM, and gesturing recognition technologies or others techniques mentioned herein where the user can change the orientation and registry of the virtual image to match the real organ. The system may utilize dynamic opacity, described below, making the AXR image either a complete view, blocking RR and the real organ, or a partial transparency, where the AXR organ image or model and the RR organ can be viewed at the same time to align them together. In this fashion, surgery precision may be increased as the areas identified in the lab on the CT or MRI can be superimposed over the real organ to know exactly where to inject, incise, resect, or otherwise operate.

The dynamic opacity subsystem that allows the system to function as a true AXR system may be provided by a multilayered lens 10, which may be part of the wearable device 1. Typically, when using a reflected image on a see-through lens in sunlight or bright light conditions, the reflected image can be washed out. Other systems solve this problem with dark lenses. Having the lens shaded all the time, however, makes the wearer vulnerable to falling or tripping over unseen obstacles. The dynamic opacity of the lens 10 of the current system, however, may only obscure that portion of the lens 10 where the eyes are viewing the AXR image as alpha matte composites, meaning the combining of several images from different sources into a single image. FIG. 8 illustrates the dynamic opacity of the present system.

The system may utilize alpha matte software that works in conjunction with eye-tracking technology and software to map the user's eye gaze and adjust not only the image, but also move or vary the opacity of the exterior of the lens 10 where the eyes are gazing, and the image is projected. In addition, the software may automatically or manually adjust the opaqueness of the alpha matte display up or down to meet ambient lighting conditions.

Figure 4:
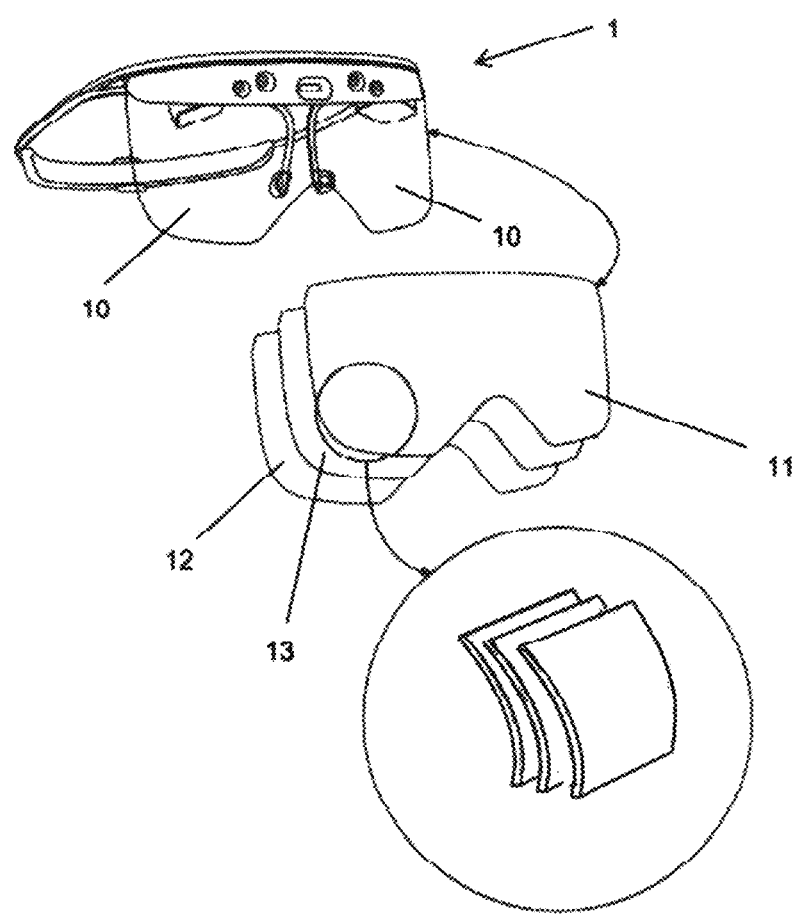
FIG. 4 is an exploded view of the lenses.

The lens 10 may have multiple layers, as shown in FIG. 4, with dynamic opacity provided on the outer layer 11, furthest from the user's eye. This layer 11 may be pixelated, which may permit the system to create a shadow or mirrored image of whatever virtual image is being displayed. This may provide a backdrop for the virtual image, blocking out light that might otherwise wash out the image. The remainder of the layer 11, where the image is not being displayed, may remain clear. Alternately, all of the pixels of the layer 11 may be activated, making the layer 11 fully obscure and blocking out the RR. This may allow the user to use the system as a VR-type headset, but with the ability to see his or her hands to pick up tools and instruments in the periphery of the glasses where the lens does not obscure the RR vision. Thus, surgeons who do not like surgery room distractions can choose to engage the dynamic opacity via voice command and make the system more like a VR headset, blocking out the view through the lens 10 behind the AXR image or video when ultra-concentration is needed. At other times, the surgeon can choose to make the dynamic opacity off or clear in the portion of the lens where there is no reflected image, to use the system in normal mode, where only the AXR image is shadowed form the back. The dynamic opacity of the lens 10 may provide a buffer between the displayed image and exterior light, giving the AXR image greater brightness to the eye. The system may allow the dynamic opacity to be enabled automatically, under pre-set conditions, manually, or with voice, gesture, or eye-tracking command.

In this fashion, the system may give the surgeon the highest RR visibility, and the added benefit of both AR and VR, so that the best of both types of altered reality is provided.

The layer 11 may comprise a plurality of pixels of cholesteric liquid crystal, each of which may be independently capable of becoming clear or opaque, or in between, as desired. In other words, the layer 11 may use electrically switchable suspended-particle smart glass based on the chiral-numatics properties of certain liquid crystals, which may not require a polarizer to achieve the alpha matte or opaqueness. The dynamic opacity, since it does not have to rely on a polarization layer, may provide gradation from and including zero to 100 percent, while it is a generally accepted scientific fact that LDC technology with polarizers can only become approximately 50% clear. This is because a system using embedded polarizers can never become 100% clear.

In suspended-particle devices (SPDs), like the layer 11, a thin film laminate of rod-like nano-scale particles may be suspended in a liquid and placed between two pieces of glass or plastic or attached to one layer without polarization or back-plane. When no voltage is applied, the suspended particles may be randomly organized, thus blocking and absorbing light. When voltage is applied, the suspended particles may align and let light pass. This dynamic opacity technology is bi-stable and is therefore highly energy efficient because the cholesteric liquid crystals do not need power to maintain a selected state like most LCD technologies, which use twisted-numatics and always need power to maintain each level of a twisted-numatic state.

The lens 10 may further comprise a reflective layer 12, which may be a lens or a coating. The reflective layer 12 may be located closest to the user's eye and may be the surface upon which images projected by the micro-displays 2 for reflection back to the user's eyes. An anti-reflective layer 13 may be positioned next and may be a layer or optical coating that may prevent unwanted artifacts, such as ghosting. The lens 10 may further comprise one or more collimators 14. The collimator 14 may be a separate layer included in the lens 10; additionally or alternately, layer 11 or layer 12 may have aspects of a collimator, and thus may function as the collimator 14; additionally or alternately, the collimator 14 may be a separate lens located between the micro-displays 2 and the reflective layer 12. The collimator 14 may be capable of concentrating rays from the micro-displays 2 in the eye box while utilizing less resolution in the periphery for an overall highest resolution and field of vision.

In one embodiment, the lens 10 may have at least three layers, including a polarized optical coating layer 12 applied to the inner surface to induce reflection and improve the contrast by eliminating stray light. This portion may contain the semi-spherical (elliptical) combiner. The middle layer may include polarization to create a perceived black. The outer layer 12 may include the dynamic opacity, which may be a pixelated layer controllable by software which induces a shadowing over the same area as the reflected augmented reality image for enhanced viewing even in bright light settings.

In the near-eye pupil forming catadioptric optical engine, wave interference may be accounted for. In the focal point, rays from a point light source may meet again and may constructively or destructively interfere with each other. Within a small region near this point, incoming light may be approximated by plane waves, which may inherit their direction from the rays. The optical path length from the light source may be used to compute this phase. The derivative of the position of the ray in the focal region on the source position may be used to obtain the width of the ray, and from that amplitude of the plane wave. The result is the spread function, whose Fourier Transform forms the optical lens design.

Also in the optical engine, the inside portion of the combiner lens 46, in the form of an optical oval (ellipse) that constitutes a mirror and has a positive focal length and is used to converge divergent beams of light into an intermediate focal distance, in this case to collect the light for the final focal distance and focused by the human eye while viewing from inside the eye-box.

The optical engine of the system may use an ellipsoidal reflector on one side of lens 46.

The AXR headset and surgical system may further comprise one or more microphones in communication with the central processing unit, where the system is capable of being controlled via voice input via the microphone, input from the eye-tracking subsystem, or a combination of voice input via the microphone and input from the eye-tracking subsystem.

The one or more microphones may be configured to create noise cancellation, or the AXR headset may include noise cancelling microphones to reduce, eliminate, or remove background noise so that the receiving person, device, or AXR headset itself can better understand the speech of the user. The wearable device may further comprise a battery and a remote communication device such that the wearable device is wireless and has communication features. The AXR headset may contain one or more batteries. In the case of more than one battery, the primary battery may be located in an external position on the headset in a manner to facilitate removal and replacement of the battery during use. The primary battery may include a mechanism for a spring-loaded battery to facilitate removal during use. In case of primary battery exhaustion, a surgery tech may press the spring-loaded battery in the back of the headset, then reattach a new, fully charged battery. The AXR headset in this instance may include a hot-swap feature, which may include one or more secondar, typically smaller, batteries, which typically would only carry enough capacity to last a few minutes. Thus, when the primary battery is exhausted, the common battery control circuit may shift to the auxiliary battery to keep the headset functioning with all features continuing until the primary battery is replaced. The system may include a battery full/battery empty capacity feature which alerts the user and others that there is only a certain about of battery charge remaining so that a timely battery change may be planned.

Figure 16:
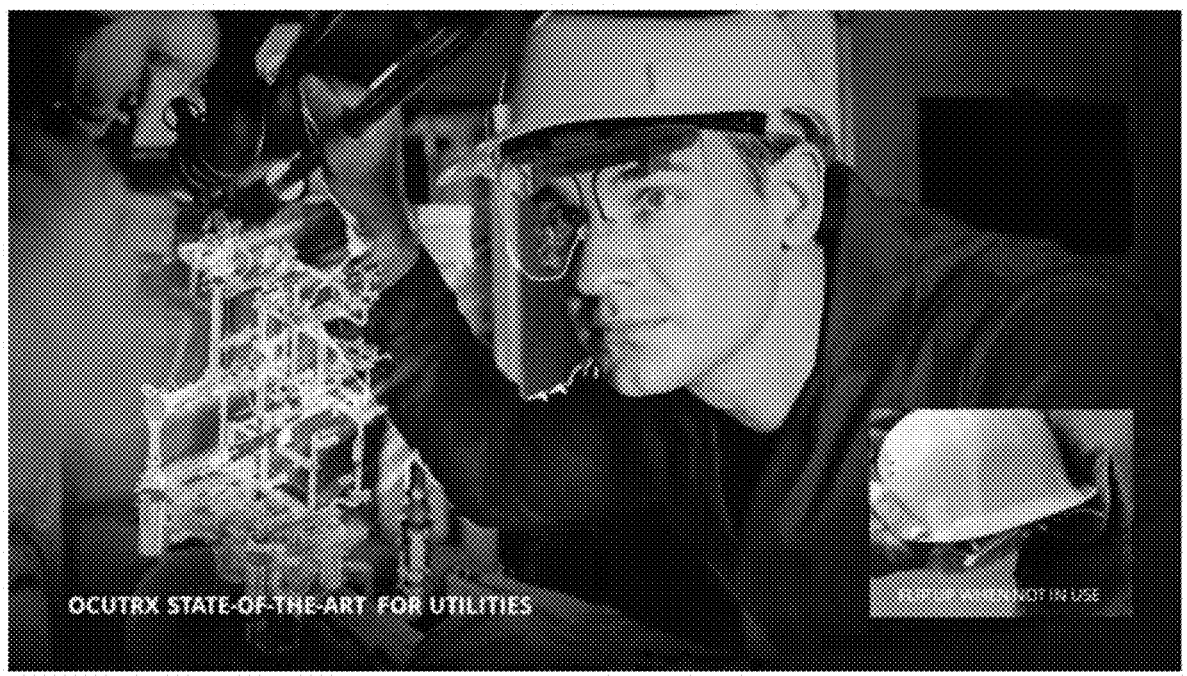
FIG. 16 is a perspective view of the AXR surgical system headset with a visor-type design.

In one embodiment, the AXR Headset 1 may have a visor design, which may be opened and raised to provide unobstructed straight-ahead view, or lowered and provide both peripheral and downward viewing beyond the lens. The system may include a clip-on corrective lens that is capable of being clipped on at the open portion of the bottom of the lens so that users with presbyopia can have their own prescription attached to the lens, such that when viewing surgery tools or other items, their own prescription is included in the view. The visor may even be cantilevered over the head, or away from the head, if necessary, in emergency situations or off surgery times, in order to provide the surgeon with an opportunity to still wear the wearable device 1, but have the visor be out of view, as shown in FIG. 16.

The 3D Autostereoscopic Monitor Technology.

The 3D autostereoscopic monitor (3DAM) 104 may comprise an LCD panel and an optical filter, where the optical filter comprises a thin substrate on which one or more optically active layers are applied. The thin substrate may be a film or a glass layer. The one or more optically active layers may comprise lenticular lenses, parallax barriers, or both lenticular lenses and parallax barriers, or have two or more layers of compressive light field displays driven by algorithms such as computed tomography, non-negative matrix factorization, and non-negative tensor factorization, or be based on volumetric reconstructed light-field display, or integral imaging, which uses a fly's-eye lens array. The monitor may also be an automultiscopic display providing a multi-view autostereoscopic 3D image to one or more viewers. In the preferred embodiment, the one or more monitors may have a native LCD or OLED or other type of active display panel and may have a resolution of 8K or higher, and the optically active layers may comprise lenticular lenses capable of producing two 4K views, one for each human eye, such that the monitor is capable of displaying a 3D image to a user without requiring 3D glasses. In addition, especially in the case of a lenticular, film or parallax barrier type monitor, it may need an enhanced back-light setting or source to off-set for any brightness diminishment due to the lenses or film described above. The back-light, which may come with a standard monitor, which may be an LED-backlit LCD monitor, which may have an in-plane switching technology leveraging liquid crystals aligned in parallel to produce rich colors may have to have its backlit panel replaced or modified to provide a higher/brighter light output meaning a higher luminance source to compensate for the lens or film dimming of the images or video.

In the preferred embodiment, the 3DAM may be mounted on a cobotic arm, may be at least an 8K resolution display with interactive 3D video images, which appear through the use of a lenticular lens or parallax barrier over an LCD, OLED, or any other emissive display technology. With an 8K image, a video feed split into right and left eye images may still be able to present a full 4K resolution to each eye. The 3D perspective source image may be brought into the system from, for example, two 4K or greater image sensors. The source images may have an angular deviation to represent the natural displacement of human eyes in order to create an apparent 3D view. Based on a few factors, including viewing angle and ergonomics, the optimal 3D viewing distance may be between 952 mm and 1200 mm.

The 3DAM may not need 3D glasses, but rather may be glasses free. It may be similar to or built from an existing monitor or television, with optical filter components added for 3D displays. Lenticular lenses or parallax barriers may redirect imagery to several viewing regions. These filters may be, in effect, beam splitters when mounted in from of an LCD display for the light exiting the panel. The filters may provide a spatially perceived view in 3D. The filters may consist of a thin substrate, for example 0.1 mm film or a 0.1 mm to 3 mm thick glass layer, on which one or more optically active layers may be applied.

Figure 19:
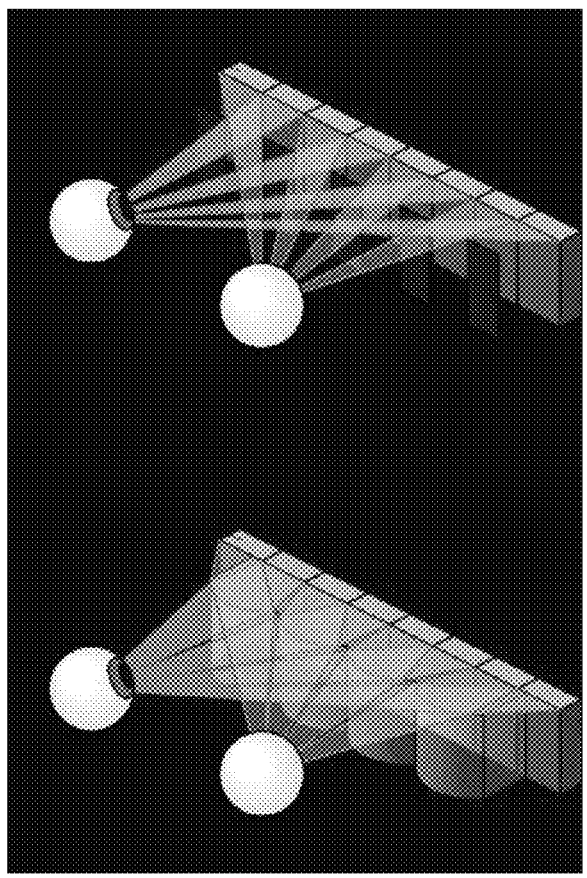
FIG. 19 is a diagrammatic illustration showing how lenticular lens placement may create a glasses-free 3D image on a television/display.

The parameters of the optically active layer(s) and the layer structure may depend on how many views one wants on the display to show 3D. In the present system, this would typically be no more than two or three display views because the more display views, the more the deterioration of the resolution. FIG. 19 shows how lenticular lens placement may create a glasses-free 3D image on a television/display.

The 8K lenticular television/display may be placed directly in front of the surgeon, allowing the surgeon to view the display without having to crane his or her neck or torso to one side or the other. The 3DADM therefore should not exceed a specified height so as to permit the surgeon to have a line of view to look directly over the 3DADM in order to get a comfortable view of the 3DAM. In this case the optics of the 3DADM may be folded one or more times.

The optical system of the autostereoscopic display may direct the pixels of the corresponding left or right image subcomponents of the 3D view to the correct eye of the user. For the user to accurately view 3D images on the autostereoscopic monitor, the source for the display may accommodate for the lenticular lenses or parallax barrier. To accommodate for the display technology, a source image may be processed via a shader, or computer algorithm, to accurately place the pixels on the display technology behind the specific optical system elements in order to present to each eye the information that allows the user to perceive 3D and depth information.

A shader is a type of computer program originally used for shading in 3D scenes, i.e., the production of appropriate levels of light, darkness, and color in a rendered image. They now perform a variety of specialized functions in various fields within the category of computer graphics special effects unrelated to shading, for example pixel placement as described above to utilize the correctly correlated optics presenting to the user's binary view. Traditional shaders calculate rendering effects on graphics hardware with a high degree of flexibility. Most shaders are coded for and run on a graphics processing unit (GPU), though this is not a strict requirement.

Shading languages are often used to program the GPU's rendering pipeline; with shaders, customized effects can be used. The position and color (hue, saturation, brightness, and contrast) of all pixels, vertices, and/or textures used to construct a final rendered image can be altered using algorithms defined in a shader and can be modified by external variables or textures introduced by the computer program calling the shader.

The 3DAM and ADMO3DV may further comprise: one or more of an eye-tracking or head-tracking subsystem associated with the monitor, such that the eye-tracking or head-tracking subsystem comprises at least one head or eye-tracking camera mounted on the monitor or monitor cobotic arm and where the head or eye-tracking subsystem is capable of tracking a user's head or eye position to keep the lenticular lenses or other 3D mechanism always in sync with the user and the user's movements via the head or eye-tracking cameras or sensors; a wireless system associated with the monitor to transmit wireless high-resolution video or images to an AXR headset; or both the eye-tracking subsystem associated with the monitor and the wireless system associated with the monitor.

The 3D Digital Viewport Technology.

The 3D digital viewport may consist of two ocular viewports existing in a housing mounted on a cobotic arm. The operator may put his or her eyes up to the eyepiece affixed to the housing and can see the wired or wireless surgery video feed in 3D stereoscopic vision emanating from the digital microscope through an optical engine, described below, which may end in a mirror that projects the 2D image to each eye stereoscopic offset to form a 3D image. The 3DDV system 106 may include eye cups such that it looks like an optical microscope viewer with fine adjustment controls.

The 3DDV mounted on a cobotic arm may move to, away, and with the operators with one or more of the described sensing and control technologies, including facial recognition, eye-tracking, head-tracking, and SLAM sensors. With these sensors mounted in the 3DDV housing, it can identify an operator of first origin, or one who has been programmed into the system. The 3DDV can move from a position of pre-programmed repose to active state where the sensors find the operators face and eyes and travel to the operator, stopping at a safe zone 16 mm from the eyes. If the operator moves his head or posture, the cobotic arm may continue to adjust through the sensing technology to move and adjust with the operator.

Figure 18:
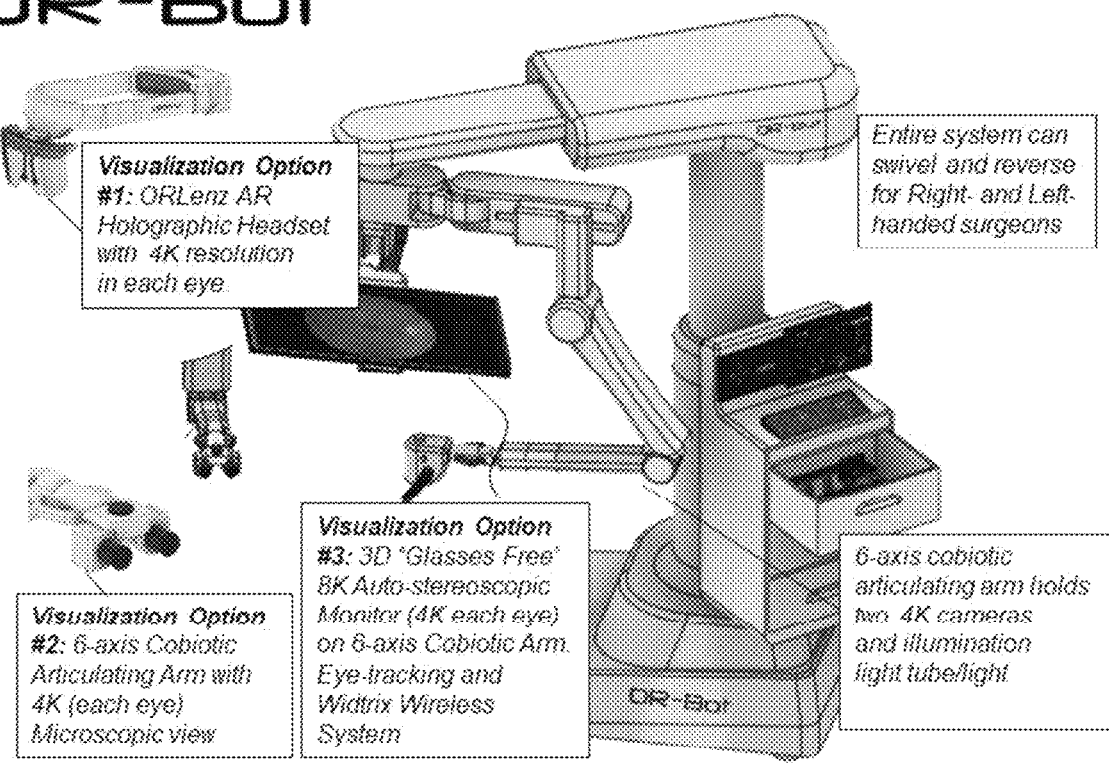
FIG. 18 is a perspective view of the surgery visualization theatre.

The 3DDV may use the same basic optical engine technology as shown in FIG. 7 for presenting a view to the operator as in the AXR headset except that instead of a conic combiner 46 at the last of the optical chain and replace that lens with a full mirror, as in FIG. 18. The converted optical engine may be housed in a casing head with eyepieces. The casing head may contain interpupillary adjustment, which may be on a worm drive and may be adjusted via Bluetooth just like the AXR headset IPD. SLAM technology and sensors may permit the 3DDV 106 to come to the surgeon's head when a voice, hand gesture, or eye-tracking cue is initiated by the surgeon. The surgeon's own individual head may be used as a fiducial marker for the 6DoF sensors to move the 3DDV system 106 to the surgeon's head until he or she directs the motion to stop. In this instance, each surgeon using the system may check into the systems and the settings saved by him or her may automatically reprogram for his or her use. Including in those personalized settings may be a 3D photograph of the surgeon so that the either through facial recognition or the combination of SLAM, 6DoF, and time-of-flight and/or ultra-sonic transducer depth estimation or LIDAR to move towards the surgeon's face. For safety, the ultra-sonic transducer may act to slow the motion towards the surgeon's face until the surgeon indicated by some means, such as voice activation, physical activation, hand gesturing, or eye-tracking. In the application of 6D0F, the surgeon's face may become a fiducial marker where the 3DDV system 106 sensors can recognize that surgeon's face as a marker and move to his or her eyes per that surgeon's pre-set preferences.

The 3D All Digital 3D Microscope.

Figure 10:
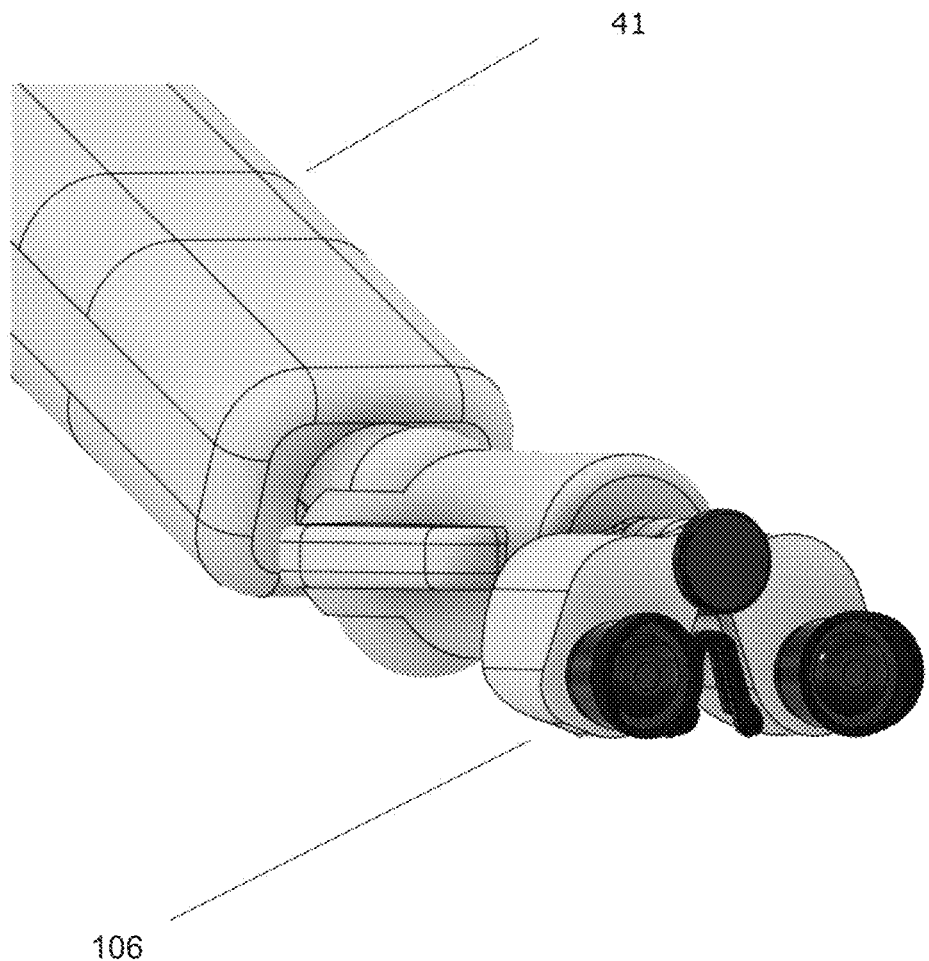
FIG. 10 is a view of the 3DDV mounted on a cobotic arm.
Figure 11:
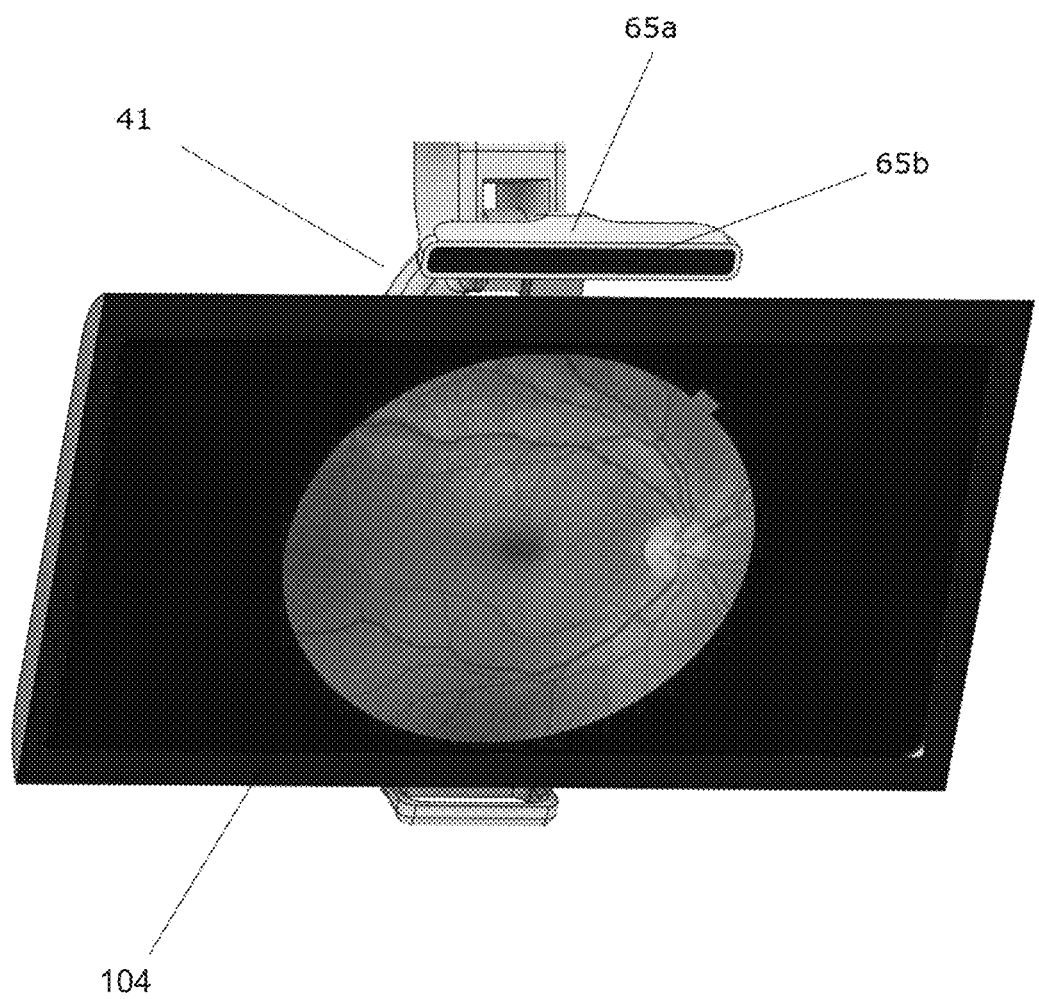
FIG. 11 is a view of the autostereoscopic 3D 'glasses free' monitor on the system.

As shown in FIG. 10, the one or more cameras 5 may alternately be housed within their own system, like the digital camera sensor 3D all-digital microscope (3DADM) system and may be connected wired or wirelessly to the AXR headset 1 and the 3DAM and 3DDV. The 3DADM system 102 may consist of two mounted cameras 5 combining parallax with optical zoom to create a 3D viewing experience and may be mounted on a six-axis robotic/cobotic arm 41 for surgery use, as shown in FIG. 11. The 3DADM may then send video over any of the methods listed in this application to the endpoint viewports. The 3DADM is called all-digital because in the preferred embodiment, it has not oculars for an eye to view optically only, though it could be configured that way, so that typically the output of the 3DADM is an image or video feed sent through wire or wireless to one of the visualization methods described herein.

The camera sensors 5 may both be 4K, 6K, or higher resolution cameras, or any other desired resolution. The digital feed may go to the six-axis robotic arm 41, which may be positioned in front of the surgeon's eyes. Inside, the surgeon may see two micro-displays 2, providing a kind of virtual reality view, but the surgeon need only move his or her head away from the microscope cups to reconnect with the real world. Micro-displays 2, such as 2560×2560 (RGB) with sizing such as 18.432×18.432 mm (1.03" diagonal) or similar, may be used to give the surgeon a full 4K viewing experience. The mechanical/optical zoom may be of any magnitude, and to the optical zoom the 3DADM may add digital zoom.

Most major surgical device manufacturers begin with legacy equipment and then add a digital component. This means typically they are less ergonomic, less dynamic, less functional, and are based on older camera/display technology. However, the 3DADM system may be all digital and may only employ ocular lenses to transfer and resolve the digital images.

The 3DADM may use cinematic full-frame camera sensors with large pixels of over six microns. For ophthalmic surgeries, light inside the retina needed for surgery with normal sensors must be very bright; however, by utilizing camera sensors with very large pixels, the light may be greatly reduced so that the retinal light toxicity is dramatically reduced.

By using these specialized sensors, which require a different and unique placement, housing, and software, the color spectrum can be increased from 1 billion potential colors to over 69 billion potential colors. This means that the cameras can differentiate colors that the human eye cannot so that the software and algorithms can be programmed to identify a particular color spectrum and that would be all cancer cells, for example, or the color spectrum could be all retinal membrane tears, which need to be removed. In this fashion, all the pixels that correspond to a particular color spectrum, and the corresponding cells which make up that spectrum, can be highlighted for a surgeon, ensuring that the surgeon gets all of that identified spectrum of cells.

At high magnification, namely 6× to 12×, the AXR headset may continually provide orientation when at high magnification levels, so the surgeon is always oriented to the unmagnified view.

In addition, the 3D ADM can provide many additional and beneficial features, beyond the reach of the legacy SOM microscopes. For instance, each of the dual sensors may be full-frame or 35 mm cinematic sensors with full 6K of resolution (6064×4040) or higher per sensor per/eye, giving a total pixel count of 24.5 million pixels per/eye throughput, or a total of 49 million pixels when viewed in 3D stereo vision with 12 bit 69 billion potential colors with 14 or higher stops.

Moreover, when the 3DADM is linked with the 3D monitor in the surgery visualization theatre, the combination can produce 10× to 90× optical/digital magnification at 4 k resolution; and 540× magnification at FHD resolution, which is still good enough resolution to clearly identify objects down to 4 to 8 microns.

The 3DADM may also contain artificial intelligence and processing software enabling pixel-shifting technologies to produce hyperacuity imaging. This may comprise a computer, mechanical, and sensor method, which may work by taking several images in milliseconds, then after each such capture moving or shifting the dual sensors to a new position. The computer may then reassemble these images, which may produce a higher resolution image or video than could be obtained on a system that does not employ these methods. The individual captures are taken at the same sensitivity; thus, the final combined image has less image noise than a single capture, making it a higher resolution image. In addition, sub-pixel shifting within the 3DADM may be used to further increase the resolution of the final image beyond the specified resolution of the image sensor.

Figure 25:
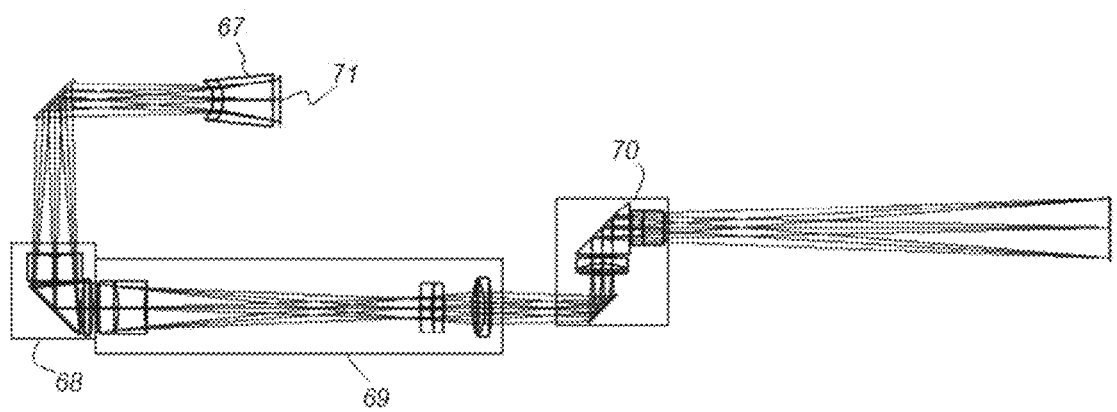
FIG. 25 is a view of the 3DADM lens system with dual optical systems.

The 3DADM lens system as shown in FIG. 25 may use dual optical systems that when combined provide a 3D image or video, each of which consists of a field lens 67 combined with a tube lens 68 and an afocal zoom relay 69 combined with an objective lens 70. This configuration forms the microscope optics transfers the image to the digital sensors 71 to create the 3D image to be seen by the user on any of the display methods set out herein, or on any other 3D display technology. This lens configuration may be folded one or more times using prisms or mirrors to conform to space requirements. Space requirements here may include that the 3DADM housing not conflict with the surgeon or user's view of the 3DAM.

Further, using pixel-shifting technologies may help in the instance of retinal surgery relating to epiretinal membranes (EPM), which are also called, when they need to be removed, an internal limiting membrane (ILM). The ILM in ophthalmology is a defect in the macula responsible for several retinal disorders, ranging from epiretinal membranes (primary or secondary to diabetic retinopathy) to retinal detachment to full-thickness macular holes, macular edema, foveal retinoschisis, and pathologies. Thus, the ILM structures which may be as small as three microns often have to be peeled by surgeons, which necessitates a surgeon clearly seeing the ILM's edges. With the 3DADM, the additional technology of sub-pixel colors and contrast modification in the software using such computer vision techniques as: thresholding, texel (a textel pixel is the fundamental unit of a texture map which are obtained through simple procedures such as thresholding) and dextel classification and modification, color detection, object detection, semantic segmentation, thresholding, and negative imaging. This is made possible by the billions of potential colors and the resolution of 3DADM which can detect colors, and differences in colors, some not even distinguishable by the human eye. Once categorized into an identifiable mapping, the model controller can highlight the edges of the ILM using a superimposed overlay on the live video feed.

The term "computer vision" is an interdisciplinary scientific field that deals with how computers can gain higher-level understanding from digital images or videos, beyond what a human can recognize or understand. The 3DADM programs tasks include methods for acquiring, processing, analyzing, and understanding digital images or video, and extraction of high-dimensional data in order to produce pixel, dexel (sub-pixel), texel, voxel (a volumetric representation of a pixel rather than a picture, which may consist of a single piece of data, such as an opacity, or multiple pieces of data, such as a color in addition to opacity), numerical, or symbolic information, which can be used as higher analysis of the real-world information for specific characteristics. As used in the 3DAMD, the software, program, and model controller may then take this information and apply it to an algorithmic logic to achieve an instantaneous new visual understanding of the image or video presented to the viewer, often one which the human eye could not detect and cannot distinguish. The enhanced image data from the 3DADM processing can take many forms, such as video sequencing, views from multiple angles or cameras, or multi-dimensional data from a 3D imaging.

Figure 17:
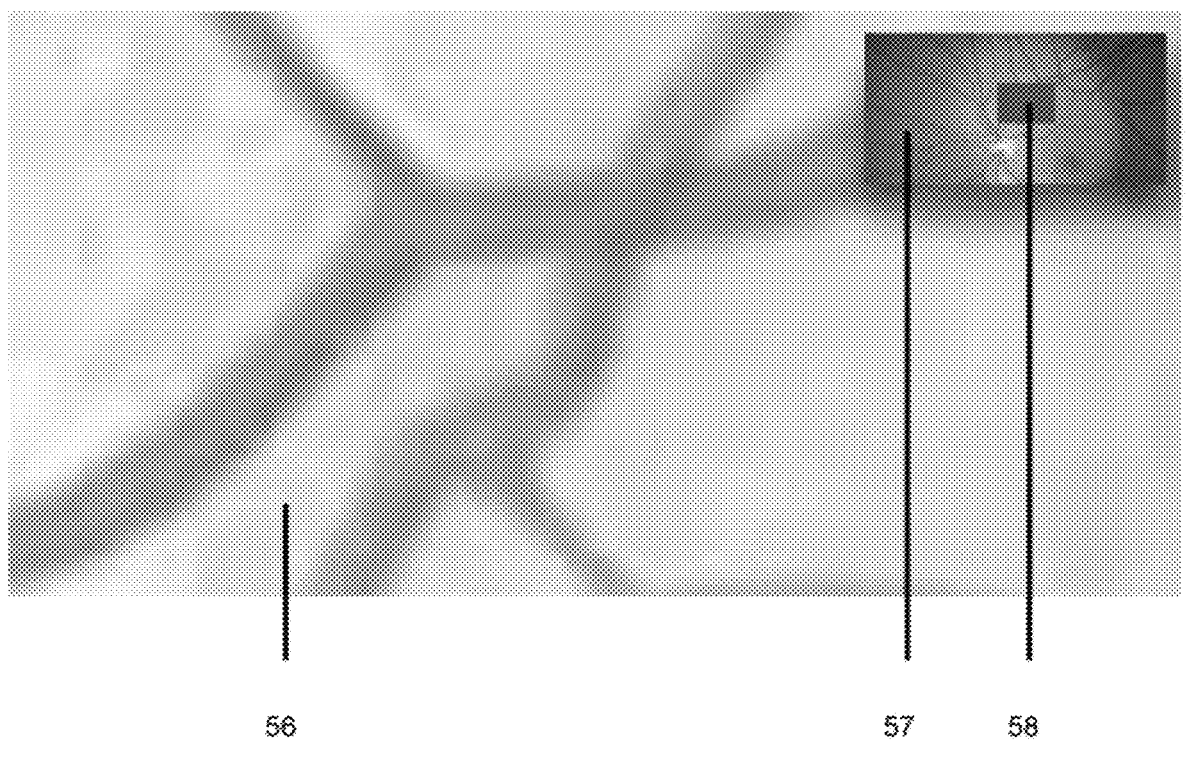
FIG. 17 is a diagrammatic view of the picture-in-picture portion of the virtual overlay software and hardware, showing a surgeon at full magnification a smaller picture of the entire FOV for better orientation.
Figure 20:
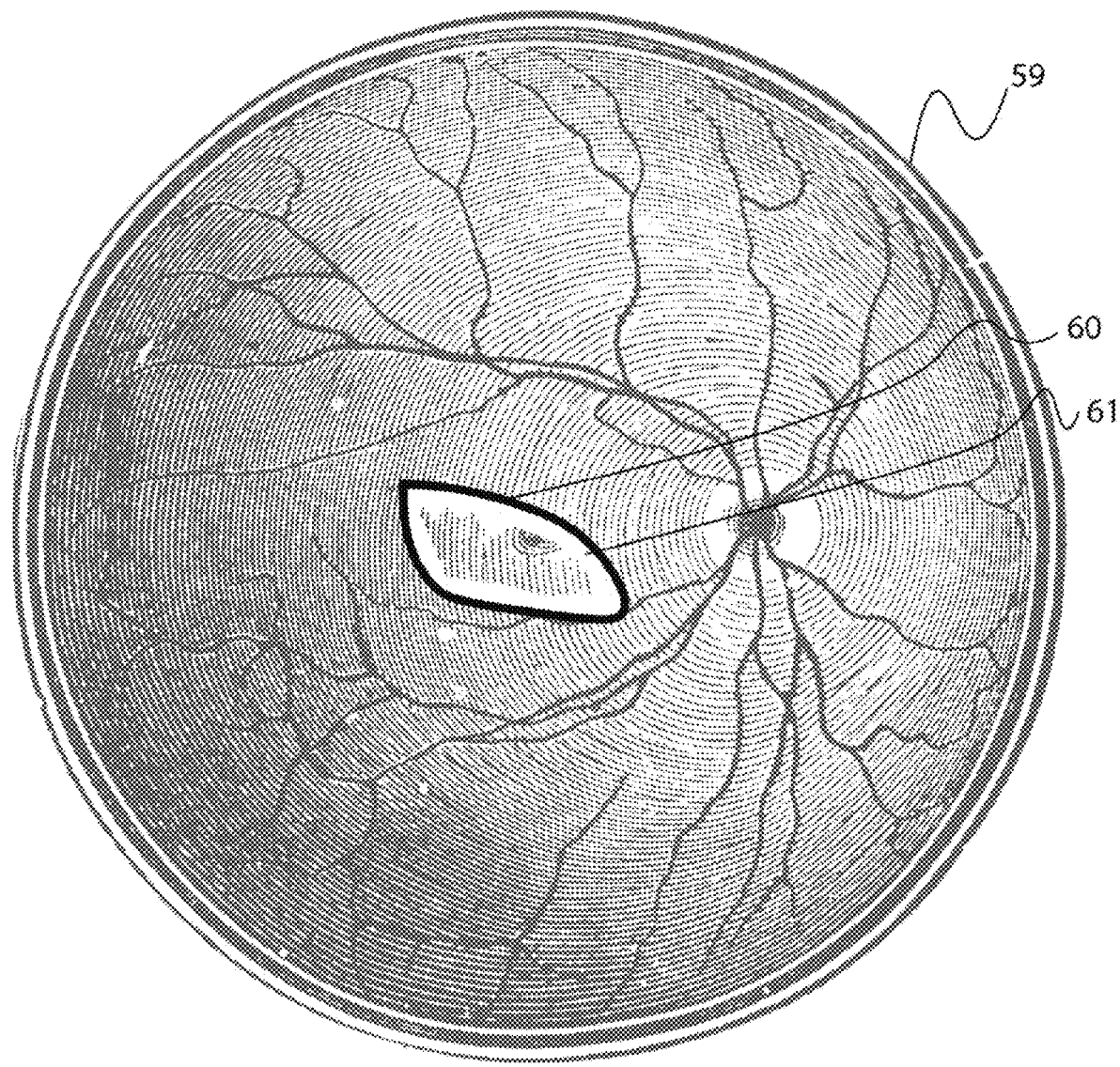
FIG. 20 is a diagrammatic illustration of the picture-on-picture superimposed imaging technology.

The 3D ADM microscope may use an additional aspect of image enhancement called aperture azimuth rotation (AAR), which in the preferred embodiment is mechanical, but which can be part mechanical and part digital or simply digital. The AAR may enable the 3DADM operator to intermittently interrupt a live surgery video feed, when activated, to take a capture of an image at zero degrees aperture azimuth, then pivot the aperture azimuth to a different degree, such as an aperture azimuth of 90 degrees, for another image capture. This may provide the 3DADM processing with images from two physical perspectives where the lighting and the actual sensor orientation captures an image from different locations. These images may then be made into a composite image and presented in one of multiple ways to the viewer, either (i) as an overlay in the streaming video, where the composite image and video feed are both seen; (ii) as a picture-in-picture, as shown in FIG. 17, shown in the area of magnification 58 in a quadrant within the video feed 57 where the composite image and video feed are both seen; 56 (hi) as a superposed image, as shown in FIG. 20, where the retina video is shown together with the highlighted the area further resolved by composite imaging overlay over the actual structure in the video feed; all herein called a superimposed overlaid image (SOI); or (iv) as a still composite image without the streaming surgery video. This process may result in a composite image, which may permit better identification of the ILM and its edges. On a surgeon's or operator's command, this superimposition can either remain in view as an overlay as outlined above, either permanently or temporarily, or be dissolved or replaced. As the surgeon proceeds with the removal of the ILM watching the 3D live video feed, the surgeon can, at any time, chose to refresh the SOI for an updated view of the remaining edges. This SOI may be repeated as many times as necessary as the surgeon continues to peel the ILM so that the edges", which have been removed and were seen in a previous SOI, are discarded and a new SOI is obtained and updated to identify the remaining areas of the edges. In addition, with the processing of the 3DADM, an operator may choose to have the software highlight the edges or object with a highlighting technology such as virtual hyper pixel colorization where all edges would look to the surgeon as another color, such as an iridescent yellow. The 3DADM may also employ AAR, which works by changing both the light distribution and camera angle from 0 degrees azimuth to 360 degrees azimuth, in separate captures throughout the degrees, which provides alternate views of the same image extending over multiple adjacent pixels. This capability enables improved 3D perception of various structures including the surface of a retina by oversampling and creating a higher resolution composite image.

SLAM technology and other sensors technologies may permit the 3D ADM to come to the surgery operative site, such as in when the 3DADM would position itself over a patient's iris for anterior or posterior eye surgery when initiated by the surgeon. The patient's head, body, face, or sub-feature, like the iris of an eye, may be used as a fiducial marker for the 6DoF sensors to move the 3DADM system to the surgery site. The fiducial markers that the system recognizes in real time may be augmented by pre-operative data, which may be pre-programmed or further adjusted by the surgeon's voice command or virtual gesture technology. Alternatively, coordinates corresponding to the exact surgery site may be feed to the ADMO3DV system to directs the motion of the 3DADM to the correct position. In this instance, each surgeon using the system may check into the systems and the settings saved by him or her and may automatically reprogram for a specific patient or set of patients to go under surgery that day. Further, as in the case of eye surgery, the ADMO3DV may be pre-loaded with target features, like iris identification technology, which may guide the cobotic 3DADM to the correct location including a 3D photograph of the patient face or body part so that the either through facial recognition or the combination of SLAM, 6D0F, and time-of-flight and/or ultra-sonic transducer depth estimation or LIDAR to move towards the exact surgery site. For safety, the ultra-sonic transducer may act to slow the motion towards the surgery site until the surgeon indicated by some means, such as voice activation, physical activation, hand gesturing, or eye-tracking takes over control of the robotic pre-programmed movement.

The Wireless Technology Subsystem.

The wearable device 1 and 23 may be lightweight and may be wireless. One of the ways to reduce weight is to have only the cameras, a battery, and sensors in the headset 1 and 23 with connectors to a WiGig®/60 GHz modem using the fastest wireless protocol available, such as the IEEE 802.1 lay protocol. Another embodiment places the intelligence in the headset 1, such as a Qualcomm® XR-2 chipset, and have the chipset circuit board be connected to a 60 GHz modem to send/receive streaming video to/from another WiGig connected location, such as a digital microscope, endoscope, or other surgery imaging device. In the case where the AXR headset receives video feed from such a surgery system, either a wire or wireless connection can be made. The ADMO3DV may have a wireless transceiver mounted in one or more places 65a and 65b which may send and receive wireless information while directed at the headset of the surgeon.

While Wi-Fi IEEE 802.11 may work, the best method would be to use a method so that uncompressed video can be sent from any image processing system to the AXR headset. In the preferred embodiment, a digital buffer may be acquired from the camera sensor as translated and augmented with the extra overlay information, if applicable, by the computer controller system, then the digital buffer may be transmitted uncompressed to receiver, which may be in the AXR headset. When the uncompressed data and buffer is received by the receiving system, it may then be translated to a pixelized image as a sequence of the streaming video. In the event of a problematic transmission where the checksum is off, then that frame may not be displayed. In addition, the program may freeze any buffered frame for hold until a valid frame was received.

In addition, the AXR headset may include a 5G modem to be capable of edge computing at multi-gigabit speeds. 5G multi-access edge computing (MEC) is a technique to migrate computing and traffic from a centralized cloud to the edge of a network, such as a localized mini datacenter where all computing is on-site or with a geolocated data center near the physical location. Data is collected and processed near the location reducing latency and providing real-time performance for high bandwidth applications. The wireless software may leverage existing wired/wireless networking infrastructure to achieve interactive low-latency peer-to-peer connections. The ADMO3DV may be connected with some or all its components and viewports to a hospital, clinic, or other 5G MEC system so that the system may support multiple online activities for multiple users and where reliability is increased, the throughput supports massive data transfers, latency is reduced, and throughput of data is increased to a projected 100 Mbps with potentially greater than 10 Gbps peak speeds. Latency is a time interval between the input to a simulation and the visual or auditory response to this input. The 3DADM system may have dual redundancy, including wire and wireless, and may comprise a sending modem in the frame of the system and a back-up unit in the camera housing.

The system may utilize a high-resolution high-speed wireless video connection from the 3D digital microscope to the AXR headset's antennae, as shown in FIG. 3, or from external sources, like being connected together with a 5G multi-access control (MEC) system with antennas located within a surgery suite or hospital or clinic with the database also inside the perimeter of the building. The 5G MEC connected to the ADMO3DV surgery system in combination with the wireless system of this invention connected between 3DDV to the AXR headset may provide crucial speed of download and uploads, critical in surgical life-threatening situations.

In this instance, since the 5G MEC is a closed system which does not permit the computing and analysis end of the transfer chain to go outside of the internally controlled system, namely the surgery suite or hospital walls, thus it can provide throughput rates with zero latency. This is compared to a typical wireless internet or cell system which may have 60 to 90 or more milliseconds or up to a minute delay and would typically have trouble with reliable downloads of compressed imagery. In this fashion, on any of the viewing options of the ADMO3DV system, when a surgeon needs to see a pre-operative 3D MRI or CT scan which was not already loaded into the ADMO3DV system, as shown in FIG. 16, the same can be presented for viewing in the most rapid method available. Internally, the ADMO3DV system may have a gateway in a combination of hardware and software so that both wired and wireless views are shown in with approximately the same latency as an actual wired HDMI system and may be synced with one or both of the wired visualization options, namely the autostereoscopic 3D monitor or 3DDV, or together with one or more wireless headsets and one or more wired display systems to present a simultaneous view on all the wireless headset(s) and wired display systems from the original camera(s) source.

The ADMO3DV controller and software may run as a bidirectional communication between a host/server and a client to transfer data, images, and telemetry information between the two devices, virtual or physical, for display on any of the viewports. The ADMO3DV controller and software may handle remote inputs, which may be sent back to the server and evaluated or executed. This may enable high-performance computing to be processed by a powerful machine remotely through the cloud or on a localized network. This methodology may work on wired, wireless, and cellular networks such as 5G. The ADMO3DV system may permit multiple users to connect to one AXR headset or the 3DADM to enable a multi-user interactive broadcast experience, such as in a teacher classroom situation where the exact same video the surgeon is seeing is what the students see. The ADMO3DV user may connect any of the components or all of them to another system and send controller data to the to the other system while simultaneously receiving bitstream audio/video output from the other system.

The ADMO3DV software may enable cross-platform users to efficiently render the incoming frames using a variety of coding libraries, such as OpenGL or Metal. The ADMO3D may support Windows, macOS, x86-64 Linux, Android, iOS, and chromeOS and can be adapted to work with future operating systems. The software currently supports up to 6 k video at 120 frames per second, but a future version could have increased resolution and frame rates. Frame rate is expressed in frames per second (FPS) which is the frequency rate at which consecutive images called frames appear on a display. Increasing the frame rate of video may divide this sequence of images into smaller periods of time, which is another method to reduce the latency and improve system performance, which is beneficial in a surgery visualization situation.

Wireless communication may also be accomplished through optical communication or through radio-frequency (RF). RF requires a transmitter and a receiver or a transceiver that incorporates both. RF communications may be used over a proprietary or a predefined protocol such as Zigbee, Bluetooth, Bluetooth Low Energy, Z-wave, or Wi-Fi. A transmitter module is an electronic sub-assembly that is capable of transmitting a radio wave and modulating that wave to carry data. A receiver module is also an electronic sub-assembly that receives a modulated RF signal and demodulates it.

The wireless technology may also employ video over IP, also called streaming, using existing standards or proprietary methods for encoding the material into a bitstream, and then using an internet protocol (IP) network to carry that bitstream encapsulated in a stream of IP packets. A bitstream is a sequence of bits. A bit is a basic unit of information in computing. A bit represents a logical state of two possible values, which are most commonly represented as a 1 or 0 or binary digit. Because of the sequential nature of the video signal, resending packets is not an option. Additional error correction information may be added to the data transmission to ensure the stream can be reconstructed even if a few packets are lost in the transfer. The surgeon may additionally or alternately wirelessly receive a 3D video feed from a digital microscope with wireless output, into the AXR headset, providing the surgeon with an alternative surgical video input.

The Eye-Tracking or Head-Tracking Subsystem.

The eye-tracking subsystem 4 of the AXR headset may work through hardware and software. The head-tracking may work similarly. The software may be connected to the system's GPU working in connection with the system's modular controller. The eye-tracking may be captured by infrared light being projected into the user's eye, which may create a glint or reflection, which may then be captured by one or more IR sensitive cameras 8. The eye-tracking subsystem 4 may be capable of capturing the glint from the eye from 30 frames per second to 500 frames per second. This information may be stored in real-time in the CPU and DSP, and then processed into a virtual space represented by x, y, z, or Cartesian coordinates. These coordinates may provide the system with the information about where the user's gaze is in relation to the reflective lens and the alpha matte layer so that both stay aligned with the user's gaze. The eye-tracking subsystem may be used to map the user's eye gaze and adjust not only the reflected images or video but also the alpha matte image located on the separate plane to keep the alpha combined image aligned with the eye box. Thus, the eye-gaze and the alpha matte layer may be controlled by the eye-tracking subsystem 4 to always stay in sync.

In addition, eye-tracking may be used as an operator command option, where an operator would look or gaze at a virtual menu projected in 3D viewports and be able to select one or more options by staring or blinking one's eye while gazing at the menu.

Further, the eye-tracking subsystem may also be used to keep the pixels in the autostereoscopic 3D monitor always aligned with the user.

Smart Pedestal Technology.

The ADMO3DV may be self-moving from one position to another pre-programmed position by using virtual track markers 112 on the floor (RFID, IR, or Optical) to accomplish its retreat from the gurney after surgery. Or if the OR team desires, it can spin 180 degrees at an out-of-the-way point and then use the fiducial markers to return to a target on the opposite side of the bed. In this fashion, the ADMO3DV can reposition itself from one side of the bed to the other. Targeting markers (on the floor) are based on optical pattern recognition technology, infrared technology, or RFID technology, which may require almost zero maintenance, provide millimeter accuracy, and take less than minutes to complete. Further, LiDAR or ultrasonic proximity sensors mounted on the system can automatically stop the unit if a person or item is in the way. In this fashion, the entire system can be programmed move into active position alongside of a surgery gurney, guided by one or more of the sensing and control techniques mentioned herein, or the ADMO3DV can automatically re-position itself to a different location for a different type of surgery or any other pre-programmed location at the command of an operator. This may result in reduced time and physical effort in the OR in transitioning from one patient to the next. It is especially helpful in the instance of a slate of cataract surgeries, so that it can move from one side of the gurney to the other automatically depending on the eye that is undergoing surgery. As it is now, if a surgery lasting 7 to 10 minutes is performed on a right eye, it may take as much as another 10 minutes to reposition the monitor after surgery if the next surgery is on the opposite eye. Further, a surgeon currently with major manufacturer's technologies has to have manually measured from his chest to the monitor the exact positioning differential to see a 4 k monitor. The ADMO3DV system may automatically move. Second, having the image in glasses worn by the surgeon is highly preferable to having to look across a patient to see a television monitor. Third, with the voice plus eye-tracking extent in the system, a surgeon is untethered from most foot pedals, hand dials, or other hardwired methods of controlling the surgery. In addition, the constant movement from a large field of vision to see the existing television screen back to near focus in a digital microscope or to hands to confirm acquisition of a tool can tax a surgeon after long surgeries or multiple surgeries in a row. With the voice plus eye-tracking of the present system and the image right in the surgeon's eyes, this issue is resolved, providing the surgeon with maximum comfort during surgeries and the least taxing method to the surgeon's eyes.

The Cobotic Arms.

The system may feature dual six-axis robotic arms which, together with the frame, may provide a huge enhancement in ergonomics and reduction of size so that the surgeon can have a painless surgery and more operating space in which to maneuver. One arm may be for the VR digital microscope viewing, while the other arm may be for the camera with folded optics. The robotic arms with their six axes may be able to reach any point in their area and remain stable with any given orientation. This is optimal for many positions needed in ophthalmic surgery, or for ear, nose, and throat surgeries, spine surgeries, or neurosurgeries.

Cobotics are the combination of robotic arms and tasks with the collaboration of an operator, here a surgeon or surgeon assistant. Thus, tasks that are arduous, difficult, or to which people add little value are transferred to machines. In the surgery context, this could be a robot arm holding a camera close to the patient's eye for potentially hours at a time, without varying or moving. Cobots may assist operators by augmenting their capabilities in terms of effort, allowing them to manipulate parts that are heavy, bulky, or too small for precision handling. Here, a surgeon or tech may start the robotic arm moving in one direction, say for instance to close it after surgery. The cobotic arm may once pushed toward a closed direction, continue to move in that direction and completely end up in the closed position. Likewise, if a surgeon or assistant pulled on the arm, it may continue until it reached a predestined spot, such as, for instance, the patient's eye. In addition, robots may be 10 times more precise than a human surgeon and may be able to make movements that are accurate within 1 micron.

The six-axis cobotic arms may be either gear and axis based articulating robotics or can be based on scara robotics. These robotic arms may combine robotic automated movement combined with the collaboration of an operator, who may activate and control the cobotic arm 41 by voice control, eye-tracking, gesture recognition, haptic technologies, touch, or other control technologies mentioned herein or with a joy-stick. Alternatively, two or more of these controls may work in combination with another for control.

The cobotic arm 41, when voice or otherwise activated using the technologies described herein, may recognize the exact site of the surgery on a patient's body to be viewed during the surgery from pre-programmed information and may travel according to the software and the ability of the six-axis arm 41 to the exact position the camera is needed for surgery. The six-axis arm 41 may be connected to a stationary or movable side-carte component stationed on the floor or connected to a boom on the ceiling or a wall.

The arms 41 may be powered by motors and may be gravity-compensated and may respond to either the touch of an assistant, or by voice command, or any other of the control technologies mentioned herein. The cobotic arms may combine axis of the scara type robotics with the six-axis gear articulating arms for the best method of gross movement combined with fine movement. The robotic arms may use gravity-neutral technologies for the compensation of gravity forces, and the forces of friction of motors and gearboxes. The low-friction, zero-gravity controller in the system may permit the guidance of the cobotic arms 41 with little effort, allowing small friction forces to reduce the free robot motion. This can serve to aid users providing different velocity profiles for different pushes.

The cobotic arm 41 may receive and transmit for instruction and feedback/tracking either sound, light, vision, movement, and/or sensitive sense-of-touch (force tactile transmission) to a remotely located user or controller in real time. The precision motors contained within the cobotic arm 41 may use the haptic sensors or internal algorithms to work with a user's so that, for instance, a slight touch in the direction of its repose may cause the cobotic arm 41 to continue to its position of repose. Likewise, if the arm 41 in in a position of repost, a slight push towards another programmed or learned location will cause it to activate the motors to continue to that location. The cobotic arm 41 may also be manually placed in a certain position by a user, and the cobotic arm's controller may remember the exact movement so that it can duplicate that movement automatically upon command by any of the technologies mentioned herein. For instance, if a cobotic arm 41 is manually placed at a surgery location needed for viewing the surgery site, and then, during the surgery the patient developed a bleed or other cause of emergency, the cobotic arm 41 could be activated to move to its repose position. Once the issue was resolved, the cobotic arm 41 with the camera may on command, return to the exact location needed to continue the surgery. Also, a surgeon or tech may slightly push the robotic arm 41 in one direction, and the cobotic arm 41 would continue to move to that direction until it ended up in the intended position. Likewise, if a surgeon or assistant pulled on an arm 41, it would continue until it reached a predestined spot.

The Multiple Overlay Visual System and Sensors.

Figure 13:
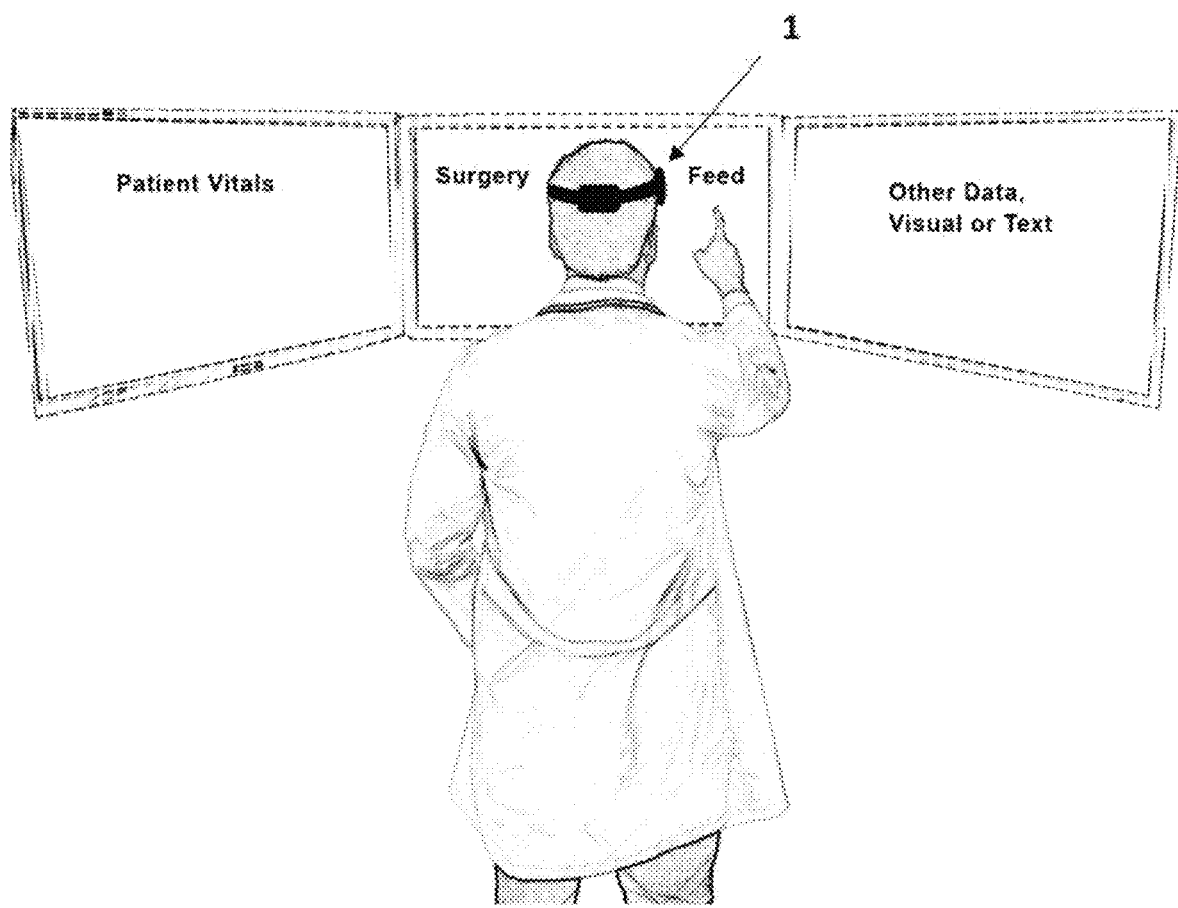
FIG. 13 is a back view of a person wearing the AXR headset, illustrating different views presented by the virtual overlay.
Figure 14:
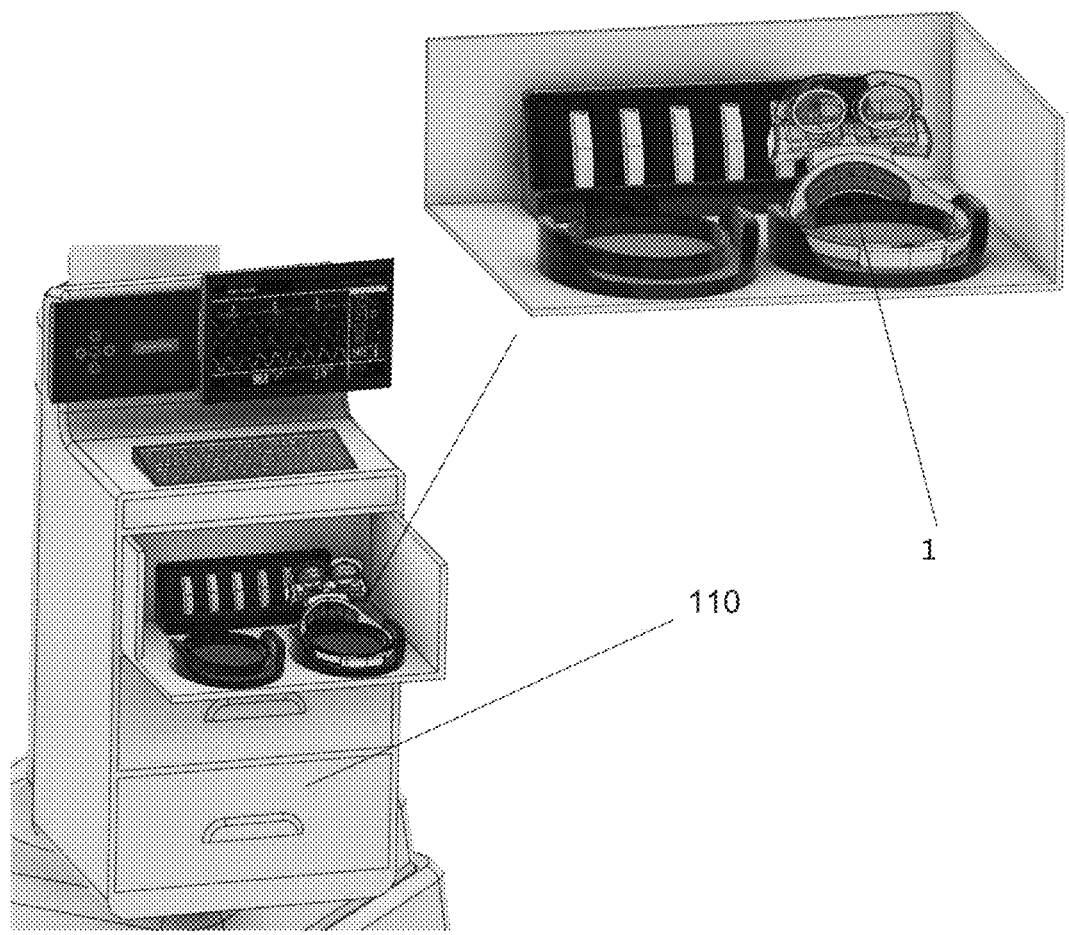
FIG. 14 is a perspective view of the charging cabinet housing the control system and computer and depicting the AXR headsets being charged and uploaded with surgery imaging data and EMR information.
Figure 15:
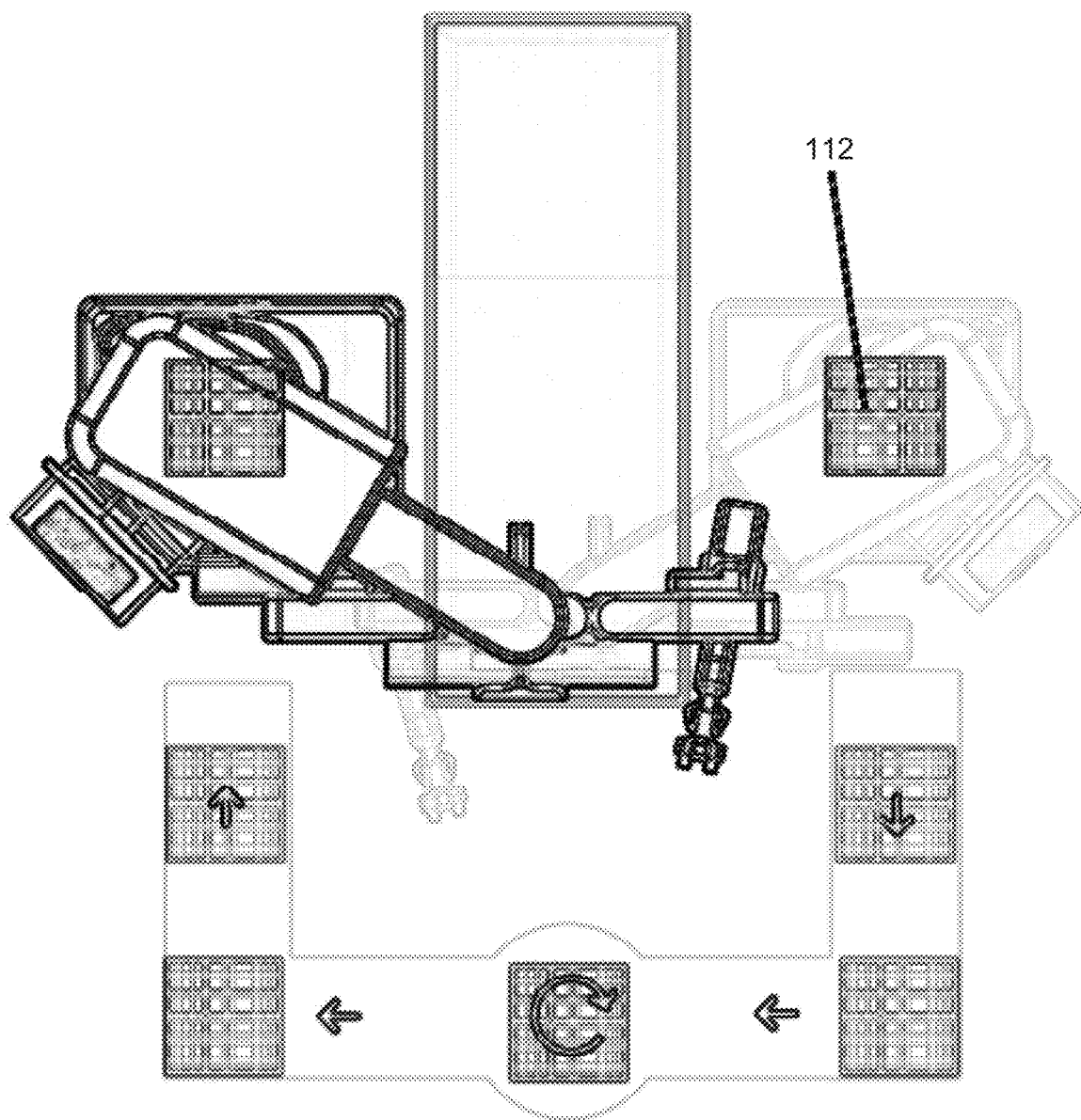
FIG. 15 is a perspective view of the smart pedestal of the surgery system showing its automatic change of position upon command.

The ADMO3DV system or AXR headset may be capable of overlaying information, such as text and graphs, in a virtual display over the operating view, as shown in FIG. 13. The system may allow the surgeon or user to control and present the overlayed information, pictures, graphs, or videos in other views inside the headset via a visual presentation subsystem. The visual presentation subsystem, powered by IMU, SLAM, and/or eye-tracking technologies, may provide an overlay of vital information, such as text and graphs, in virtual display over the 3D operating view. The visual presentations may be like windows or chyron generated view visible within the AXR FOV and may be virtually presented in a certain pre-set location of the user's view. For example, for an ophthalmologic surgery, the system may display intraocular pressure, cut rate, and flow rate or may show which mode a surgeon is in, such as vitrectomy, extrusion, dense tissue, etc., and may retrieve and track a preloaded surgery plan. For other surgeries, such as vascular, ENT, thoracic/cardiac, or orthopedic, this information displayed may vary depending on the equipment or information useful to the surgeon during the surgery.

Alternatively, the overlay may be used to view preoperative or interoperative images in virtual format, including pictures, videos, MRI's, CT scans, and the like. This information may be visible upon voice command of the surgeon, and the system may provide the user the option of displaying information at the bottom, side, or top of the AXR lens view. In other words, for example, if using eye-tracking or head tracking, the surgeon may move his or her head or eyes at a predetermined degree of rotation, for instance 15 or 30 degrees either to the side or up and down. With this turn of the eyes or head, the surgery video feed images may disappear and alternative information like patient vitals may appear. When the surgeon moved his or her head or eyes the opposite way, equipment readouts, preoperative information, or other important information may appear. Likewise, when the surgeon moves his or her head or eyes back, the surgery images may appear to return focus to the surgery. When the surgeon looks a certain pre-set degree downward, the surgery images may disappear, and the surgeon could refocus on the RR patient and surgery. Alternately, the system can be set to leave the information always in view. Thus, a surgeon who does not like distractions can have the option of making a slight head or eye adjustment as needed to see the information. For example, while a retina surgeon is in laser mode, he or she may enable the information display to show power, standby versus on, duration, and intensity.

The system or 3DADM may also provide for intraoperative optical coherence tomography (iOCT). While typically there is a need for a technician to also be in the room to assist with the iOCT's operation, the system may replace the technician with its voice plus eye-tracking commands.

Optionally, the AXR headset may use IMU, SLAM, eye-tracking, and/or other technology to permit the surgeon to move his or her head forward or use an eye movement or other manner of control described herein to cause the z coordinate to reorient to magnify or reduce the surgery image.

For the system to provide these options, the AXR headset 1 may be embedded with SLAM, 6DOF, inertial measurement units (IMU), or eye-tracking technology, which may interpret the angle of the user's head or eyes versus the displayed image. Then, when either the eyes or head move to focus on a portion of the image that is originally on the edge of the view, the system may digitally reposition the image to the center of the user's visual field, providing a high-focus view independent of where the image was originally located.

The head tracking subsystem 3 may include an internal array of IMUs 7, which may include one or more accelerometers, gyros, and/or magnetometers. Using these sensors, the system may be capable of automatically enabling and switching between camera systems depending on the position of the surgeon's head. For example, when the surgeon looks down, the system may enable the front-facing cameras 5, and then when the surgeon looks up or straight ahead, the system may enable the downward cameras 5 to permit the surgeon to comfortably find a forward-looking position while the downward facing cameras 5 capture the surgeon's hands and the operating space. Upon a voice command issued from the surgeon, the system may switch off the RR cameras 5 and convert to projecting the images from a scope or digital microscope.

The accurate alignment of AXR images with RR images may be achieved by using AI and a set of trackers 6, which may be used to determine the exact position of the cameras 5 and the patient's body. The AI engine together trackers 6 may identify and track fiducial markers placed on the surface of specific structures that remain still during surgery, such as iliac crest, clavicles, etc., and thus provide the system with points of reference. The system may take the fiducial marker information and fuse it with other inertial measurement data, which may be provided by the internal array of inertial measurement units 7, to provide a stable localization of the overlay system. The system may utilize proprietary 2D/3D software maximized for surgery.

The system may include a six degrees of freedom (6DoF) sub-system capable of providing real-time interfacing and no time loss between accessing 3D-type CT or MRI scans and projecting those images for surgery. The 6DoF sub-system may allow the system to pin 2D and 3D images to a virtual marker in virtual space. The 6DoF sub-system may comprise a high-performance tracking system driven by multiple sensors and cameras, including a ToF camera and high camera-frame-updating-rate (>90 fps) and global shutter features. This may keep SLAM tracking positions and 3D virtual images in the right place at all times, with little to no drift. This may ensure, in a surgery application, that a virtual MRI of a heart stays locked in place when the surgeon looks for other views, or when looking away from the surgery to speak to a technician.

The system may be capable of displaying CG images over the top of pass-through RR. This may include presenting images generated using a fusion of optical images with near-infrared fluorescence images not visible to the human eye. These images can provide more useful immediate feedback that is overlayed in context to what is needed, such as blood flow. This technique may be used to increase precision by providing additional data for the surgeon to consider. Using this technique, surgeons could be able to detect blood vessels under the organ surface or detect other tissue abnormalities.

The system may be used as a digital magnifier, providing up to 12× magnification with both near-field viewing and wide-field viewing.

Figure 21:
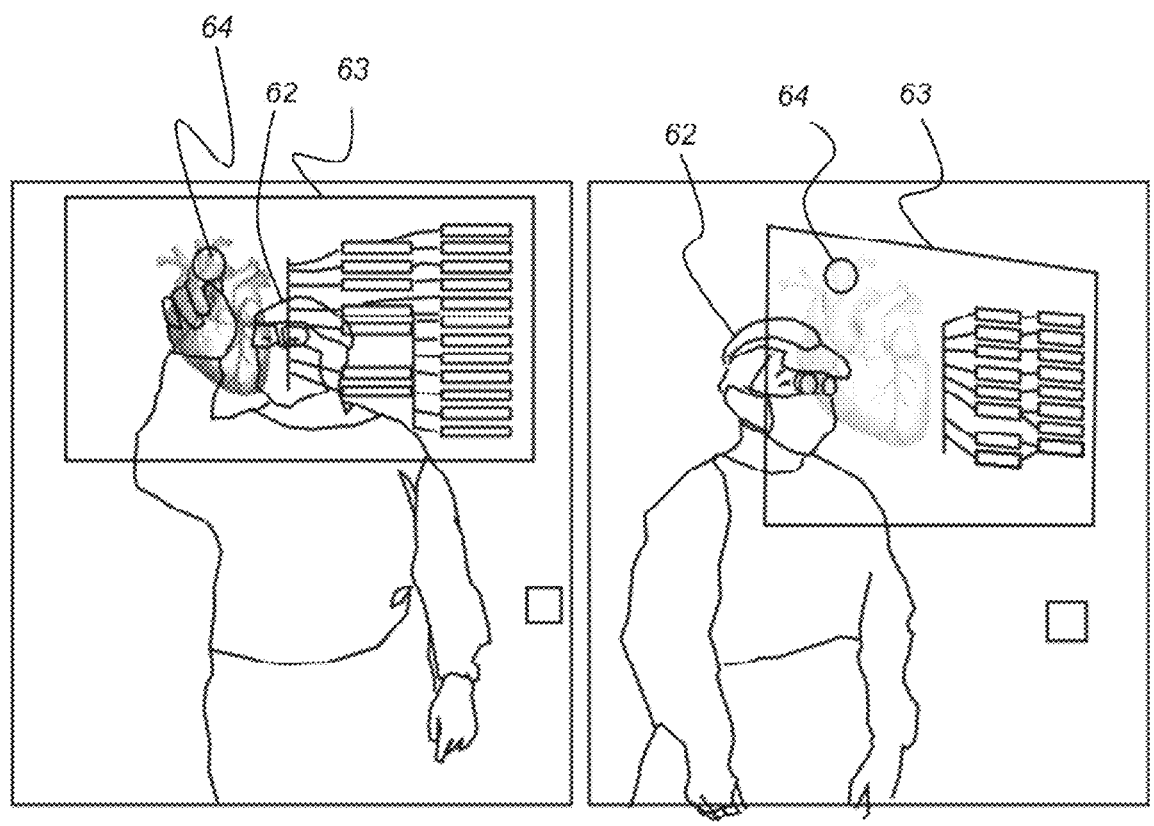
FIG. 21 is a diagrammatic illustration of the remote surgery assist feature with both surgeons seeing the same virtual information and area of interest.

As noted above and shown in FIG. 21, the system may be in communication with one or more second systems such that one or more remote users 62 can view the same images 63 from the system on the one or more second systems and communicate will the user and other remote users and together focus on a common area of interest 64. The AR headset can be worn at the surgery site or remotely providing multiple parties with a real-time experience of the surgery to all headset wearers. By utilizing gesturing recognition and other mentioned technologies embedded in all user's headsets, any number of wired or wireless connected, or networked users may see the same virtual image. Then, any connected user can point to a specific point or set of points, or define one or more areas in virtual space, on the commonly seen virtual image in all the user's AXR headsets, which may then communicate and correspond that same reference information into the view of a select set or all other user's AXR headsets or to any other monitors and displays in the network. This technique may work with either a current simultaneous view or a current or past picture or video feed. Since the controller on all connected and simultaneously viewing headsets knows exactly where each pixel exists in the displayed virtual image, it may be able to identify the specific point or set of points, or area or areas, of interest and transmit that information wirelessly, or over a wired connection, to create a corresponding marker on all connected user's headsets so that all connected users can see and understand the specific point, set of points, area, or areas of interest originated by the initial pointing user. Likewise, the point or set of points or area or areas commonly displayed may be used as a point of reference or a measurement. In addition to images, any textual, graphical, or other information may also be commonly viewed by connected users. In addition, any connected AXR headset user using the technologies mentioned herein or through AI techniques may choose to view commonly displayed 2D or 3D images or 2D or 3D models in the same perspective as another; or any user may choose a different perspective of the same 2D or 3D images or models.

Optical Frequency Wireless

Low latency video transmissions may be required for useful video streams for real time surgery. This latency may be defined as less than 20 ms. Uncompressed video data transmission may be required to achieve these latency numbers. Typical wireless video transmissions may include some amount of compression so as to fit the entire video stream in the usable throughput of the data transmission system. The incorporation of certain data transmission technologies, however, may allow a much higher amount of data to be available for the transmission of high-resolution video. Using a free space optical system, the system may achieve data rates high enough to transmit uncompressed video data, which can be in excess of 20 Gbps for true stereo 4K video with 10-bit color. The system may utilize multiple optical receivers on the headset, which may each have a different range of directionality so as to have a wide field of reception. The system may also utilize a transmitter that utilizes head tracking in real time in order to align the relatively narrow beamwidth of the transmitter to the receiver array on the headset. In another embodiment of the invention, a system could be used that utilizes active alignment on both the receiver and the transmitter.

In one embodiment, the head tracking may be obtained using input from the camera and computer vision algorithms to determine the identifiable shape of the head to give the location and rotation of the head in space. In another embodiment, the head tracking may be obtained utilizing input from a camera and computer vison algorithms to track a passive fiducial marker, or array of passive fiducial markers, to determine the location and rotation of the head in space. By utilizing these novel ideas of near free space optics, the system may achieve a high availability, high throughput system capable of transmitting true stereoscopic uncompressed video. The antenna positioning for the modem could also be improved by using this idea of active antenna motion. When used with a headset with multiple receivers, each of which have a different range of directionality, and a transmitter that is positionable in real time with regards to the headset, and in conjunction with head tracking technologies, the system may be able to always keep the transmitter aligned to the headset using a pan and tilt system.

Picture-In-Picture Technology.

When the user begins to zoom in or magnify an image, a picture-in-picture may appear, which may allow the user to keep their orientation and understand where they are located within the whole image, as shown in FIG. 18.

Picture-in-picture technology in the ADMO3DV system may permit a user of any of the viewports to watch two images or videos (primary and secondary) simultaneously. The primary picture 56 may fill the entire screen or projection across a lens, while the secondary picture may be a smaller (approx. 1/4th of the primary picture size), floating window pinned to a corner of the screen (always on top of all other windows), which may allow users to keep an eye on what is happening in both images at one time. The primary picture may be a digital image created by the 3DADM and viewed in any of the viewports. The 3DADM may have the ability to magnify or zoom up to 12× with 2× optical and 6× digital magnification. The original digital signal may always be maintained the in software, as the increased magnification may be a digitally enhanced copy of the primary picture, once the user begins to zoom, the image or video on the lens may become the primary picture, and a smaller screen may appear as the secondary picture. The centers of two related maps may indicate the same x, y, z coordinates. A secondary picture map 57 may represent the area on a smaller scale, and while the primary picture may be a digitally magnified image of the area of interest, the secondary picture may remind the operator where he is in the big picture.

This utility is designed to simplify identifying where the viewer is in relation to the non-zoomed image. This feature may permit the user to examine the same region of the image with different zoom levels with respect to the whole image before it was magnified. Through software and the controller, each picture may be a dynamically linked map that follows along the same coordinates. Changing the coordinates of the center on one of them may lead to an automatic displacement of the center in the same point of the second and a coordinate display unit informs of the current coordinates. Thus, when a user begins to magnify or zoom in on an image or video, a secondary picture may appear on the lens of the viewport and the larger, magnified image may become the primary picture. The primary picture may be magnified as specified by the user while the secondary picture may capture the original coordinates of the primary picture before it was magnified. Through software control and menu selection, the secondary picture can be pinned to either the top left corner, top right corner, bottom left corner, or bottom right corner depending on the surgeon's preference, and can be shifted to a new location using virtual touch commands.

The secondary picture may function as a magnifying glass. In fact, there may be no image enhancing; for example, a utility for determining the coordinates uses the same data source, but not limited to the magnification of the image. The secondary picture may simultaneously capture the close-up area represented by the primary picture indicated by a 40% transparent grey shaded square called the "Magnification Identifier" that is overlaid on top of the zoomed-out image. The user may be able to identify their location in the primary picture relative to the secondary picture as it is indicated by the grey shaded square 58.

The secondary image may be a digitally altered sub sampling of the primary image. Thus, the secondary image may fill the viewport showing a surgeon their region of interest, while the primary image may be placed in a corner of the viewport to serve as a map. The position of the secondary image may then be indicated on the primary image via an overlay, whether varying capacity monochrome or color. Digital altering of the primary image can include digital zooming, color contrast enhancement, color picking, or other video processing system that is useful for the surgery.

The AI and Big Data Technology.

One of the features of an all-digital system which can self-record all information and imaging is the brand-new patient and surgery data to be collected and analyzed and the introduction of artificial intelligence (AI) into the surgery headset. The surgery visualization unit may provide an unparalleled opportunity to get in on the ground floor of the data revolution where the data from surgeries can be collected and categorized in order to analyze and improve ophthalmic and other surgeries.

"Big data" refers to the interdisciplinary analysis of high volume, diverse clinical and patient information. The ADMO3DV system may house, send, and receive EMR information and imaging for surgery.

The use of such data in surgery has the potential to improve outcomes, increase safety, improve surgeon accuracy, and aid surgery planning.

The creation and analysis of vast amounts of data from the recorded video of the surgeries may integrate into a data plan at the outset of a ADMO3DV development program to alleviate some of these surgery pain points by enabling innovation, guiding regulatory pathways, and maximizing commercialization opportunities.

Big data analytics in surgery is currently in a nascent stage, however, this will not be for long. Many organizations will want to take advantage of the data collected during a surgery, especially video data which has the potential to be critically analyzed. Also, the advent of AR in the surgery room presents a new opportunity for the advanced organization to begin now to devise and combine the 3D and 4D imaging of radiologist with and AR surgeon experience.

The ADMO3DV can connect surgical quality improvement efforts with pre- and post-surgical care and linking up with quality improvement efforts in primary and nonsurgical specialty disciplines.

For instance, the ADMO3DV can take advantage of the herein described advances in computers' screens and visual perception and can record and analyze the outcomes so that this process can be one which can be repeated and learned by the surgeons and the headset. To reduce risks, the augmented reality image can show the surgeon the exact correct position of the surgical tip tool, so that risk can be reduced, and surgery outcomes enhances.

Using AI techniques embedded in the AXR headset or in a repository or neural network in communication with the one or more AXR headsets, through wired, wireless, or over 5G Edge Computing connections, one or more current or stored surgery videos or still images can be analyzed and compared against a data model or composite of data models to find either specific or general information based on specific criteria, and show a result as a virtual image(s) on one AXR headset in real-time or on a plurality of connected AXR headsets Alternatively, the AI engine may make a similar comparison with a number of specific criteria's or no criteria at all, and bring novel information inferred from the system.

Using these technologies, for instance, a 3D MRI virtual image of an organ could be managed or compared with AI by one of the techniques set out herein in virtual space by the surgeon without getting contaminated by touching a real object, in order to change the registry and orientation of the virtual organ image to match the RR organ to increase the surgeon's understanding of where to incise, inject, or perform some other similar surgical act. In the case of the manipulation of a virtual image to match a real image, as stated above, the system may increase or decrease the opacity gradient of the lenses, so that both the virtual organ and the real organ may be viewed, or aligned, by the surgeon seeing them both at the same time.

The system can be an effective tool for training and skill assessment of surgery residents, other medical staff, or students. Specialized training simulators that can interject unusual or emergency situations may be created and used to improve surgeons' skill in various scenarios, as well as to objectively measure their technical skills. The system may prove especially beneficial for trainee residents and students in developing intuition and proper decision-making abilities, which can otherwise be only gained through long clinical practice.

While the instant invention focuses on the medical applications, the same technology may be used in other sectors, where a user needs to have a primary view and the ability to have other reference views available. Further, where this invention states words like "surgeon" or "assistant" or "tech" this is used in the common context of surgery application, but the same function and features apply to anyone wearing the AXR headset.

Improvement Over Existing Systems.

It has been widely accepted that to change to digital from optical, surgeons want to see at least 4K resolution. However, existing systems do not offer 4K resolution to the surgeon's eyes. They may offer a 4K television/display, but the feed from the cameras is only 1080p resolution. Further, because 3D glasses need two different inputs out of 4K, the resolution of the screen is halved. What the surgeon sees in each eye is one half of 4K or 1920×1080 resolution. The present system may improve on both technologies with two 4K micro-cameras, which may feed into an 8K television/display and create better depth of field, as well as providing true 4K resolution. Since 4K is four times the resolution of full HD, then 8K is double the resolution of 4K and 16 times the resolution of full HD (7680×4320). This is a difference the surgeons will recognize and appreciate.

Further, existing systems use passive 3D glasses, which means they are polarized. The LCD lenses in the 3D glasses are, at best, only 50% transparent. Thus, half of the brightness of the tv/display light is lost as it comes through the 3D LCD glasses lens. The present system may use an 8K autostereoscopic 3D lenticular display, as described above, which is a lens-free approach and provides the surgeon with a heads-up display that is fully 3D from the distance of the system to the surgeon.

Also, existing systems use HDMI cables to send the digital microscope feed, producing a 10-millisecond lag time in the digital video, which is an issue with some surgeons. The present system, on the other hand, may bring 5G and above wireless video to the operating room. The wireless technology described herein may send dual 4K video at speeds faster than HDMI.

Existing systems have television monitors separate from the tools control, creating at least a 15-minute time frame to move to the opposite side of the table for right/left eye in surgery. This may cause surgical backlogs and impact how many patients can be operated on in a day. The present system, however, may provide an ergonomic placement of the television/display so that the surgeon can look straight ahead, whether he or she selects the headset or 3D television/display. This placement may work for both vitreoretinal surgeons as well cataract surgeons and may give them the option of a 3D television display of the digital surgery feed or being able to wear the AXR headset. The present system thus may radically reduce time in back-to-back opposite eye surgeries while providing better ergonomics for the surgeon.

By using the six-axis robotic arms instead of traditional hanging mechanisms, the area in front of the surgeon may be almost free space, a far cry from the bulk of existing systems. In addition, cameras may have horizontally folding optics so that less space in front of the surgeon's hands may be occupied with system gear. The optional digital microscope view arm may likewise swing out of the way if the surgeon is using the 3D television/display or the headset or can swing into position for an assistant or other surgery member to use.

As such, the present invention may provide three visualization options, as shown in FIG. 18. The first visualization option may be the AR holographic headset with 4K resolution in each eye; the second visualization option may be the six-axis cobotic articulating arm with microscopic view with 4K resolution in each eye; and the third visualization option may be the 3D glasses-free 8K autostereoscopic monitor, providing 4K resolution to each eye, on a six-axis cobotic arm, with the eye-tracking and wireless subsystems. Another six-axis cobotic articulating arm may hold two 4K cameras and lights for illumination. The entire system may be able to swivel and reverse for right- and left-handed surgeons.

AXR Headset as Eye Protection During Laser Surgery.

The AXR headset 1, combined with the surgical digital microscopes' feeds and laser technologies for treatment of conditions in the eye, may provide surgeons with enhanced surgery visualization, ease, comfort, and safety. Medical lasers, including ophthalmic lasers, provide precise treatment for a range of eye conditions with little risk of infection and are usually a less invasive option. The combination of safety, accuracy, and relative low cost makes lasers very useful ophthalmic tools for such surgeries as a posterior capsulotomy. Ophthalmic lasers are used with patients who have previously had cataract surgery then present with subsequent cloudy vision due to clouding of the posterior capsule. A surgeon uses a laser to painlessly clear the vision again. Other ophthalmic laser uses include treatment of glaucoma, diabetic retinopathy, vein occlusions, retinal holes, and retinal detachments. The Code of Federal Regulations (CFR) Part 1040 in the US and IEC 60825 internationally, defines "classes" of laser depending on their power and wavelength and protection needed.

When medical lasers are used, there exists a nominal hazard zone (NHZ) in an operating room, where personnel must adhere to appropriate eye protection procedures during all laser applications. Appropriate laser protective eyewear (LPE) must be worn by everyone in the NHZ while the laser is in operation. Appropriate LPE typically currently consists of glasses or goggles of sufficient optical density (OD) to prevent ocular injury at the laser wavelength in use. Surgeons looking through a microscope which has a lens filter for the laser in use are typically exempt, but now with the advent of new head's-up tv monitor surgery systems, this often also includes the surgeon who must wear protection. This means a surgeon may have to hold the laser while a tech removes his 3D glasses and puts on goggles, all while the surgeon is holding the place to laser.

The AXR headset 1, however, may double as the safety protection for laser surgery. In this way, surgeons, assistants, techs, and others in the OR NHZ wearing the AXR headset 1 may not have to wear googles because the dynamic opacity lens features may serve to safely block harmful laser photons and wavelengths through film or optical filters or dynamic opacity. As noted above, the dynamic opacity layer may contain cholesteric liquid crystals on the outer lens, which may create a shadow opaqueness that exactly (1:1) mirrors the image being projected onto the reflective inner lens. In this way, the lens can be up to 85 percent see-through so very little ambient lights has to be blocked, whereas other AR headsets must block up to 85 percent of ambient light to see the AR image. Unlike other liquid crystal technologies, the dynamic opacity may be characterized as bistable because their liquid crystals do not need power to maintain a selected state. This is not true of LCDs or LEDs because LCDs need constant power. Also, LCDs, because they use polarization, can only be 50 percent see-through, while cholesteric liquid crystals provide the ability to be almost 100 percent see-through. Testing shows that the cholesteric liquid crystals hold significant promise in blocking and attenuating photons emitted by medical lasers. Current tests show blocking of almost 70 percent of direct laser hit with reflection and diffusion of the intensity of the laser beam with just a few crystals, with improvements on the crystal layers resolution and wave filtration expected in the future.
Remote Medical Presence and Remote Patient Monitoring.

The AXR headset 1 may be used to allow healthcare practitioners to deliver care and services virtually via remote medical presence (RMP). The headset 1 may allow for real-time video chatting between a patient and a healthcare professional; WiFi VOIP or cellular voice connection; in excess of 4K resolution for both the professional and the patient; the healthcare professional to view virtual readouts of vitals while watching the patient; the healthcare professional to view the patient's other healthcare records viewable on the medical professional's headset 1; and real-time access to patient vitals. Patient vitals that may be obtained with the AXR headset 1 may include heart rate; respiratory rate and respiratory effort; blood pressure; temperature; pulse oximetry; visual field testing; eye-tracking; rOTC; functional outcome measurements in addition to visual acuities such as contrast sensitivity, visual field, and reading speed; and other real-time testing. Patient generated data may be sent or hosted on HIPAA-compliant secured communications and clouds with encryption. A clinical portal may be offered in conjunction with the AXR headset, offering users a simple, intuitive, and efficient system. Patents may be able to use the portal to see and chat with their doctors in real-time. Sensors in the AXR headset may provide some of the patent vitals, while Bluetooth-connected device tools may permit patents to measure other vital statistics at home, such as weight and ECG. The system may allow for secured messaging without providers having to provide personal cell numbers to patients, as well as smart alerts that automatically ping the physician based on patient vitals.

Generally speaking, the terms remote medical presence (RMP) or remote patient monitoring (RPM) refer to the use of digital technologies to collect health data from an individual in one location and electronically transmit that information securely to a healthcare provider in a different location for assessment and recommendation. AR/RMP means remote patient monitoring with an AR headset on each end. The AR format may provide a convenient, more cost-effective system to allow the healthcare provider to monitor a multitude of patients efficiently between visits. Healthcare providers may have better control of a patient's acute or chronic conditions. Remote patient monitoring, home care, and telehealth have been gaining traction as a healthcare offering due, in part, to the needs of an aging population, which increasingly views these kinds of options as a means of avoiding age-related in-office hardships, such as transportation, stairs, parking issues, and the physical rigor of receiving regular check-ups.

The RMP system of the present invention may operate over WiFi or cellular systems and may be completely HIPPA compliant, allowing secure patient communications between the patient and healthcare provider and 5G video and communications. From the physician's standpoint, all of the patient's vital signs may show up in a virtual readout on the side of the lens, which the provider can see and review to diagnose from, all while communicating with and watching in real-time the patent virtually in the headset. From the patent's standpoint, benefits of the RMP system may include better patient engagement, better patient accountability, easier access to healthcare, healthcare in a comfortable environment, social distancing compliance, improved quality of care, peace of mind and assurance, and improved support, patient education, and feedback.

Physically, the RMP system may utilize the AXR headset 1 with sensors in the headset 1 to measure certain vitals, with WiFi or cellular connection, such that the results in real-time from the patient vitals sensors may be sent to the healthcare provider for review virtually on the healthcare provider's AXR headset 1. The patient can either stand in front of a mirror, where the two 4K front-facing cameras may pick up the reflected image, or the patient can attach a camera extension, namely a camera on a flex cable that connects through a micro-USB connection at the top of the AXR headset 1. The camera flex extension may be used in order to look back at either the patent or the healthcare provider, or the patient can use the reverse camera to look at other parts of the body where there is an issue, like the hands or feet.

Additionally, the eye-tracking cameras may be used to view the eyes for injury or problem, or another set of color camera may be attached on the reverse of the AXR headset 1 to a place like the top of the nosepiece or the lenses, for a reverse look at the face. Images from two or more cameras may be digitally stitched together to make one comprehensive picture.

In another embodiment of the invention, the RMP system may have one or more micro-mirrors in the collector lens, each of which may receive and reflect a stream of laser beam mounted in the headset to project into the eye for optical coherence tomography for measuring the back of the eye. In this fashion, the remote optical coherence tomography (rOCT) system may use light waves to take cross-section pictures of the patient's retina. As the rOCT scan progresses, the result of the scan may be recorded in the headset 1 and transmitted over WiFi or cellular RF to be interpreted at the ophthalmologist office. With rOCT, the ophthalmologist may remotely see each of the retina's distinctive layers. This may allow an ophthalmologist to map and measure their thickness from software that receives the raw information from the remote AXR headset 1. These measurements may help with diagnosis and treatment, as well as guidance for treatments for glaucoma, macular degeneration, RP, diabetic eye disease, and diseases of the retina.
Virtually Modified Face Telecon Visualization.

Knowing that it is comforting to people to speak face-to-face and given an instance of necessary isolation of people due to disease or mitigating factors, the AXR headset 1 may be used to enhance the feeling of comfort, trust, and communication using video facial presence. It is good for this facial presence to be two way as a normal face-to-face conversation. One of the benefits of using the AXR headset 1 is that the user may constantly have the facial presence presented. In bidirectional communication mode, each participant may be both a viewer and a subject/presenter.

A complication of presenting a pleasing visual presence is that the user has the headset on his or her face. One iteration to overcome this distraction is to start with a digital snapshot of the subject/presenter without the headset on. This snapshot may become the basis of the subject's presentation face, a large portion of which normally would not change in the video from frame to frame. What does change, normally, are the eyes, the mouth, and various cheek and forehead muscles. The amount of change from frame to frame may be minimized even more since the headset and cameras are mounted on the subject's head, meaning the relation of camera view to subject remains the same even though the subject may be walking or moving his or her head around.

In this instance, eye tracking cameras or additional cameras mounted in a similar location may be used to digitally modify the presented face, the changing content focused mainly on the areas with the highest probability of change, i.e., the mouth and the eye region. The changes may be digitally integrated with the whole face view to create a composite view of the face, seen virtually without a headset on.

In video compression, there is a well-known method to only update the parts of the motion video that are changing or that have a delta from frame to frame. This invention may work along the same principles but by integrating a whole face/background facial image with the live emotional content variations from eye movements and other active regions.

Face Mask Addition to AXR Headset for Protection/Clean Air Supply.

A clip-on face mask may be used to enhance the AXR headset 1 for operation in questionable or contaminated spaces. The face mask may be a typical N1 filtration capability mask or may use photocatalytic (UV energized titanium dioxide coated surface) active pathogen oxidation techniques. The system may use a combination of photo-catalytic pathogen oxidization in combination with post filtration to capture any spuriously created ozone before inhalation. Whereas, the devices and methods have been described in relation to the drawings and claims, it should be understood that other and further modifications, apart from those shown or suggested herein, may be made within the spirit and scope of this invention.

Remote Medical Presence-Telehealth Application of the AXR Headset

In another aspect, the invention relates to a remote medical presence system comprising a patient augmented/extended reality (AXR) headset and a medical provider augmented/extended reality (AXR) headset, where each of the patient AXR headset and the medical provider AXR headset comprises: one or more micro-displays; one or more lenses, where the micro-displays are capable of projecting images onto the lenses; one or more cameras; and a communication system, such that a patient wearing the patient AXR headset and a medical provider wearing the medical provider AXR headset can communicate remotely in real time via the AXR headsets.

Generally speaking, the terms remote medical presence (RMP) or remote patient monitoring (RPM) refer to the use of digital technologies to collect health data from an individual in one location and electronically transmit that information securely to a healthcare provider in a different location for assessment and recommendation. AXR/RMP means remote patient monitoring with an AXR headset on each end. The AXR format may provide a convenient, more cost-effective system to allow the healthcare provider to monitor a multitude of patients efficiently between visits. Healthcare providers may have better control of a patient's acute or chronic conditions and know better when a patient should come into the doctor's office or a hospital, or remain at home.

Remote patient monitoring, home care, and telehealth have been gaining traction as a healthcare offering due, in part, to the needs of an aging population, which increasingly views these kinds of options as a means of avoiding age-related in-office hardships, such as transportation, stairs, parking issues, and the physical rigor of receiving regular check-ups. Even in the U.S. it is becoming increasingly difficult for those in need of healthcare to access their preferred physicians. Doctor's office trips also involve parking costs, often negotiating large building complexes and time spend waiting in medical offices. Remote medical presence may help reduce the costs and effort of travel to a healthcare provider's office and bring immediacy to the patient and diagnosis right from their own homes.

In addition to better access to care, patients may also enjoy an improved quality of care, due to the RMP monitoring and AR advances. Not only can they connect instantly and directly with their physicians, but also enjoy less wait times, or getting stuck in traffic or the emergency room.

The micro-displays may each be capable of 4K resolution. The communication system may comprise WiFi VOIP or cellular voice connection. Each AXR headset may further comprise a head-tracking subsystem, an eye-tracking subsystem, and a central processing unit in communication with and capable of controlling the micro-displays, lenses, cameras, head-tracking subsystem, and eye-tracking subsystem. The eye-tracking subsystem may comprise one or more rearward-facing cameras capable of capturing images of a user's eyes.

The medical provider AXR headset may be capable of displaying patient vitals and/or patient medical records to a user of the medical provider AXR headset while simultaneously displaying an image of a user of the patient AXR headset. Sensors in the AXR/RMP may provide patient vitals to the doctor, but also record them for the patient to review at any time. Bluetooth-connected device tools may permit patients to measure other vital statistics at home, like weight and ECG. Secured messaging may be sent between the two AXR/RMP headsets (doctor and patient) without providers having to provide personal cell numbers to clients. Smart alerts may be sent by the patient or doctors about check-ups, need for a remote call, or just automatically sending patient vitals to the physician's headset or patient software portal. Moreover, with the AXR/RMP headset, a van or bus can be converted and sent to underserved areas and by wearing the headset for diagnosis, sometime with multiple patients in one vehicle, the patient can have vital signs checked and visual field test taken while wearing the headset all while the attending physician is remote, yet instantly reviewing the results for analysis, diagnosis, and treatment.

The patient AXR headset may further comprise one or more patient vitals sensors capable of sensing one or more patient vitals. At least one of the one or more patient vitals sensors may be mounted within the patient AXR headset, and/or at least one of the one or more patient vitals sensors may be physically separate from the patient AXR headset but connected to the patient AXR headset wirelessly. The one or more cameras of the patient AXR headset may comprise a camera on a flex cable connected to the AXR headset. The patent AXR headset may further comprise one or more micro-mirrors capable of receiving and reflecting a stream of laser beam mounted in the headset to project into a user's eye for optical coherence tomography.

Collected patient data may be sent to or hosted on a HIPAA-compliant database or secured communications and cloud computing with encryption. The AXR/RMP may offer clinical portal users a simple, intuitive, and efficient system. Patients can see and chat with their doctors in real-time and exchange voice and data medical information.

Whereas, the devices and methods have been described in relation to the drawings and claims, it should be understood that other and further modifications, apart from those shown or suggested herein, may be made within the spirit and scope of this invention.

What is claimed is:

1. An augmented/extended reality (AXR) headset for use with a surgery visualization system, comprising:
   a wearable support frame;
   one or more forward-facing cameras pivotably mounted to the wearable support frame;
   an imaging system mounted to the wearable support frame and including:
   an image generator configured to form a 2D image; and
   a catadioptric optics assembly including:
   a partially transmissive curved mirror positioned in front of a wearer's eye;
   a beam splitter positioned between the partially transmissive curved mirror and the viewer eye; and
   an optical image relay configured to conjugate the 2D image formed from the image generator to a curved focal surface of the partially transmissive curved mirror and including a prism having a fold surface configured for folding the optical path for light generated by the image generator towards the beam splitter; and
   a control logic processor coupled to the one or more front facing cameras and the image generator, and programmed to execute an algorithm including the steps of:
   receiving image data from the one or more forward-facing cameras; and
   operating the image generator to display the received image data onto the curved mirror.

2. The AXR headset of claim 1, wherein the one or more forward-facing cameras is configured to rotate downward to a position substantially 90 degrees from a plane of a front of the AXR headset.

3. The AXR headset of claim 2, wherein the one or more forward-facing cameras is configured to rotate between about 60 to 90 degrees.

4. The AXR headset of claim 1, wherein the one or more forward-facing cameras includes a 4K resolution camera.

5. The AXR headset of claim 4, wherein the one or more forward-facing cameras is configured to capture a wide field-of-view between about 180 to 210 degrees forward-facing vision.

6. The AXR headset of claim 1, further comprising a first imaging system associated with a left eye of the wearer and a second imaging system associated with a right eye of the wearer.

7. The AXR headset of claim 6, further comprising an interpupillary distance (IPD) adjustment system coupled to the first and second imaging systems for adjusting a distance between a first partially transmissive curved mirror and a second partially transmissive curved mirror.

8. The AXR headset of claim 1, further comprising an outer lens mounted to the wearable support frame such that the partially transmissive curved mirror is positioned between the outer lens and the wearer's eye.

9. The AXR headset of claim 8, wherein the outer lens includes a plurality of layers including a dynamic opacity layer.

10. A method of assembling an augmented/extended reality (AXR) headset for use with a surgery visualization system, including the steps of:
    providing a wearable support frame;
    coupling one or more forward-facing cameras to the wearable support frame such that the one or more forward-facing cameras are pivotable with respect to the wearable support frame;
    coupling an imaging system to the wearable support frame, the imaging system including:
    an image generator configured to form a 2D image; and
    a catadioptric optics assembly including:
    a partially transmissive curved mirror positioned in front of a wearer's eye;
    a beam splitter positioned between the partially transmissive curved mirror and the viewer eye; and
    an optical image relay configured to conjugate the 2D image formed from the image generator to a curved focal surface of the partially transmissive curved mirror and including a prism having a fold surface configured for folding the optical path for light generated by the image generator towards the beam splitter; and
    coupling a control logic processor to the one or more front facing cameras and the image generator, the control logic processor programmed to execute an algorithm including the steps of:
    receiving image data from the one or more forward-facing cameras; and
    operating the image generator to display the received image data onto the curved mirror.

11. The method of claim 10, wherein the one or more forward-facing cameras is configured to rotate downward to a position substantially 90 degrees from a plane of a front of the AXR headset.

12. The method of claim 11, wherein the one or more forward-facing cameras is configured to rotate between about 60 to 90 degrees.

13. The method of claim 10, wherein the one or more forward-facing cameras includes a 4K resolution camera.

14. The method of claim 13, wherein the one or more forward-facing cameras is configured to capture a wide field-of-view between about 180 to 210 degrees forward-facing vision.

15. The method of claim 10, wherein coupling the imaging system to the wearable support frame includes:
    coupling a first imaging system associated with a left eye of the wearer to the wearable support frame; and
    coupling a second imaging system associated with a right eye of the wearer to the wearable support frame.

16. The method of claim 15, including the step of coupling an interpupillary distance (IPD) adjustment system to the first and second imaging systems for adjusting a distance between a first partially transmissive curved mirror and a second partially transmissive curved mirror.

17. The method of claim 10, including the step of coupling an outer lens to the wearable support frame such that the partially transmissive curved mirror is positioned between the outer lens and the wearer's eye.

18. The method of claim 17, wherein the outer lens includes a plurality of layers including a dynamic opacity layer.

* * * * *